(12) United States Patent
Gottesman

(10) Patent No.: US 11,432,769 B2
(45) Date of Patent: *Sep. 6, 2022

(54) SYSTEM AND METHOD FOR PHYSIOLOGICAL MONITORING

(71) Applicant: Janell M. Gottesman, San Francisco, CA (US)

(72) Inventor: Janell M. Gottesman, San Francisco, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 14/680,280

(22) Filed: Apr. 7, 2015

(65) Prior Publication Data

US 2015/0208986 A1    Jul. 30, 2015

Related U.S. Application Data

(62) Division of application No. 13/238,957, filed on Sep. 21, 2011, now Pat. No. 9,017,256.

(Continued)

(51) Int. Cl.
| | | |
|---|---|---|
| *A61B 5/00* | (2006.01) | |
| *A61B 5/02* | (2006.01) | |
| *A61B 5/0205* | (2006.01) | |
| *A61B 5/11* | (2006.01) | |
| *A61B 5/0245* | (2006.01) | |
| *A61B 5/145* | (2006.01) | |

(Continued)

(52) U.S. Cl.
CPC .......... *A61B 5/6833* (2013.01); *A61B 5/0002* (2013.01); *A61B 5/0205* (2013.01); *A61B 5/02028* (2013.01); *A61B 5/1118* (2013.01); *A61B 5/486* (2013.01); *A61B 5/6823* (2013.01); *A61B 5/6869* (2013.01); *A61B 5/7282* (2013.01); *A61B 5/742* (2013.01); *A61B 5/0245* (2013.01); *A61B 5/02405* (2013.01); *A61B 5/08* (2013.01); *A61B 5/14532* (2013.01); *A61B 5/14546* (2013.01); *A61B 5/318* (2021.01); *A61B 5/4035* (2013.01); *A61B 5/4839* (2013.01); *A61B 2503/40* (2013.01); *A61B 2560/0412* (2013.01); *A61B 2562/0219* (2013.01); *A61B 2562/164* (2013.01)

(58) Field of Classification Search
CPC .......... A61B 5/0002; A61B 2560/0412; A61B 5/1118; A61B 5/0205; A61B 5/6833
See application file for complete search history.

(56) References Cited

U.S. PATENT DOCUMENTS

| | | |
|---|---|---|
| 4,219,019 A | 8/1980 | Coates |
| 4,989,607 A | 2/1991 | Keusch et al. |

(Continued)

OTHER PUBLICATIONS

R. Picard and J. Healey, "Affective wearables", Personal Technologies, vol. 1, No. 4, pp. 231-240, 1997. Available: 10.1007/bf01682026 (Year: 1997).*

(Continued)

*Primary Examiner* — Lynsey C Eiseman
*Assistant Examiner* — Amanda L Steinberg

(57) ABSTRACT

Apparatus, systems, and methods for monitoring a sensor module mounted in a sensor platform, wherein the sensor platform includes an adhesive side and a pocket, wherein the pocket is designed to receive the sensor module, to facilitate sensing by the sensor module of physiological attributes, and to allow insertion and removal of the sensor device from the pocket.

6 Claims, 23 Drawing Sheets

Related U.S. Application Data

(60) Provisional application No. 61/385,266, filed on Sep. 22, 2010.

(51) Int. Cl.
| | |
|---|---|
| *A61B 5/318* | (2021.01) |
| *A61B 5/024* | (2006.01) |
| *A61B 5/08* | (2006.01) |

(56) References Cited

U.S. PATENT DOCUMENTS

| | | | |
|---|---|---|---|
| 5,090,410 | A | 2/1992 | Saper et al. |
| 5,209,230 | A | 5/1993 | Swedlow et al. |
| 5,393,798 | A | 2/1995 | Weber |
| 5,480,717 | A | 1/1996 | Kundel |
| 5,665,477 | A | 9/1997 | Meathrel et al. |
| 5,694,939 | A * | 12/1997 | Cowings .............. A61B 5/486 600/484 |
| 6,144,868 | A | 11/2000 | Parker |
| 6,212,427 | B1 | 4/2001 | Hoover |
| 6,358,201 | B1 * | 3/2002 | Childre .............. A61B 5/024 600/300 |
| 6,564,079 | B1 | 5/2003 | Cory et al. |
| 6,605,046 | B1 | 8/2003 | Del Mar |
| 6,845,272 | B1 | 1/2005 | Thomsen et al. |
| 6,986,747 | B2 | 1/2006 | McCulloch et al. |
| 7,163,512 | B1 | 1/2007 | Childre et al. |
| 7,330,752 | B2 * | 2/2008 | Kettunen .............. A61B 5/024 600/508 |
| 7,379,764 | B2 | 5/2008 | Schmid |
| 7,689,285 | B2 | 3/2010 | Garabet |
| 7,691,049 | B2 * | 4/2010 | Wood .................. G16H 20/30 600/26 |
| 8,306,610 | B2 * | 11/2012 | Mirow .................. G16H 10/20 600/509 |
| 8,636,670 | B2 | 1/2014 | Ferren et al. |
| 9,017,256 | B2 | 4/2015 | Gottesman |
| 2003/0009092 | A1 | 1/2003 | Parker |
| 2003/0149344 | A1 * | 8/2003 | Nizan .................. A61B 5/6887 600/300 |
| 2003/0149349 | A1 | 8/2003 | Jensen |
| 2003/0214408 | A1 | 11/2003 | Grajales et al. |
| 2004/0030258 | A1 | 2/2004 | Williams et al. |
| 2005/0085751 | A1 | 4/2005 | Daskal et al. |
| 2005/0113646 | A1 | 5/2005 | Sotos et al. |
| 2005/0240114 | A1 * | 10/2005 | Elliott .................. A63B 23/185 600/520 |
| 2005/0245793 | A1 | 11/2005 | Hilton et al. |
| 2006/0064037 | A1 * | 3/2006 | Shalon .................. G16H 20/60 600/586 |
| 2006/0100534 | A1 | 5/2006 | Colombo et al. |
| 2006/0173247 | A1 | 8/2006 | Medina |
| 2007/0050150 | A1 * | 3/2007 | Levy .................... G16H 20/70 702/19 |
| 2007/0100218 | A1 | 5/2007 | Sweitzer et al. |
| 2008/0045808 | A1 | 2/2008 | Hassonjee et al. |
| 2008/0086064 | A1 | 4/2008 | Rembrand et al. |
| 2008/0125288 | A1 | 5/2008 | Case |
| 2008/0183053 | A1 | 7/2008 | Borgos et al. |
| 2008/0287747 | A1 | 11/2008 | Mestrovic et al. |
| 2009/0076345 | A1 | 3/2009 | Manicka et al. |
| 2009/0163781 | A1 | 6/2009 | Say et al. |
| 2009/0177068 | A1 * | 7/2009 | Stivoric .................. A61B 5/01 600/365 |
| 2009/0182204 | A1 | 7/2009 | Semler et al. |
| 2009/0201172 | A1 | 8/2009 | Edell |
| 2009/0240193 | A1 | 9/2009 | Mensinger et al. |
| 2009/0254404 | A1 * | 10/2009 | Eggenberger .... G06Q 10/06398 705/7.14 |
| 2009/0292180 | A1 * | 11/2009 | Mirow .................. G16H 10/20 600/301 |
| 2009/0299301 | A1 | 12/2009 | Gottlieb et al. |
| 2009/0323067 | A1 | 12/2009 | Medina |
| 2010/0174205 | A1 * | 7/2010 | Wegerif .............. A61B 5/02405 600/515 |
| 2010/0312188 | A1 | 12/2010 | Robertson et al. |
| 2010/0324427 | A1 * | 12/2010 | Devot .................. A61B 5/0205 600/484 |
| 2012/0071731 | A1 | 3/2012 | Gottesman |
| 2012/0123220 | A1 | 5/2012 | Iyer et al. |

OTHER PUBLICATIONS

"U.S. Appl. No. 13/238,957, Advisory Action dated Dec. 12, 2014", 3 pgs.

"U.S. Appl. No. 13/238,957, Examiner Interview Summary dated Dec. 2, 2014", 3 pgs.

"U.S. Appl. No. 13/238,957, Final Office Action dated Jul. 31, 2014", 14 pgs.

"U.S. Appl. No. 13/238,957, Non Final Office Action dated Nov. 8, 2013", 13 pgs.

"U.S. Appl. No. 13/238,957, Notice of Allowance dated Jan. 5, 2015", 13 pgs.

"U.S. Appl. No. 13/238,957, Response filed Feb. 10, 2014 to Non Final Office Action dated Nov. 8, 2013", 10 pgs.

"U.S. Appl. No. 13/238,957, Response filed Jul. 12, 2013 to Restriction Requirement dated Jun. 13, 2013", 8 pgs.

"U.S. Appl. No. 13/238,957, Response filed Dec. 1, 2014 to Final Office Action dated Jul. 31, 2014", 12 pgs.

"U.S. Appl. No. 13/238,957, Restriction Requirement dated Jun. 13, 2013", 7 pgs.

"Sesium: product overview", [online], [retrieved on Aug. 13, 2010]. Retrieved from the Internet: <URL: http://www.toumaz.com/public/page.php?page=sensium_intro>, (2010), 1 pg.

Parmar, Arundhati, "St. Jude Medical reinvests in iRhythm Technologies", [Online]. Retrieved from the Internet: <URL: http://www.minnpost.com/medcitynews/2011/05/16/28311/st_jude_medical_reinvests_in_irhythm_technologies>, (May 16, 2011), 2 pgs.

Queen, D., "Technology update: Understanding hydrocolloids", [online], [retrieved on Sep. 20, 2010]. Retrieved from the Internet: <URL: http://www.woundsinternational.com/article.php?issueid=1&contentid=129&articleid=229>, (Sep. 11, 2009), 8 pgs.

Sussman', G., "Technology update: Understanding foam dressings", [online], [retrieved on Sep. 20, 2010]. Retrieved from the Internet: <URL: http://www.woundsinternational.com/article.php?contentid=129&articleid=8816&page=1&print>, (Sep. 2, 2010), 5 pgs.

Porges, Stephen W., "The Polyvagal Theory: phylogenetic contributions to social behavior", Physiology & Behavior 79, (2003), pp. 503-513.

Porges, Stephen W., "Vagal Tone: A Physiologic Marker of Stress Vulnerability", Pediatrics, vol. 90, (Sep. 3, 1992), pp. 498-504.

McCraty, Rollin, et al. "The coherent heart near-brain interactions, psychophysiological coherence, and the emergence of system-wide order." Integrae Review: A Transdisciplinary & Transcultural Journal for New Thought, Research, & Plan's 5.2(2009).

* cited by examiner

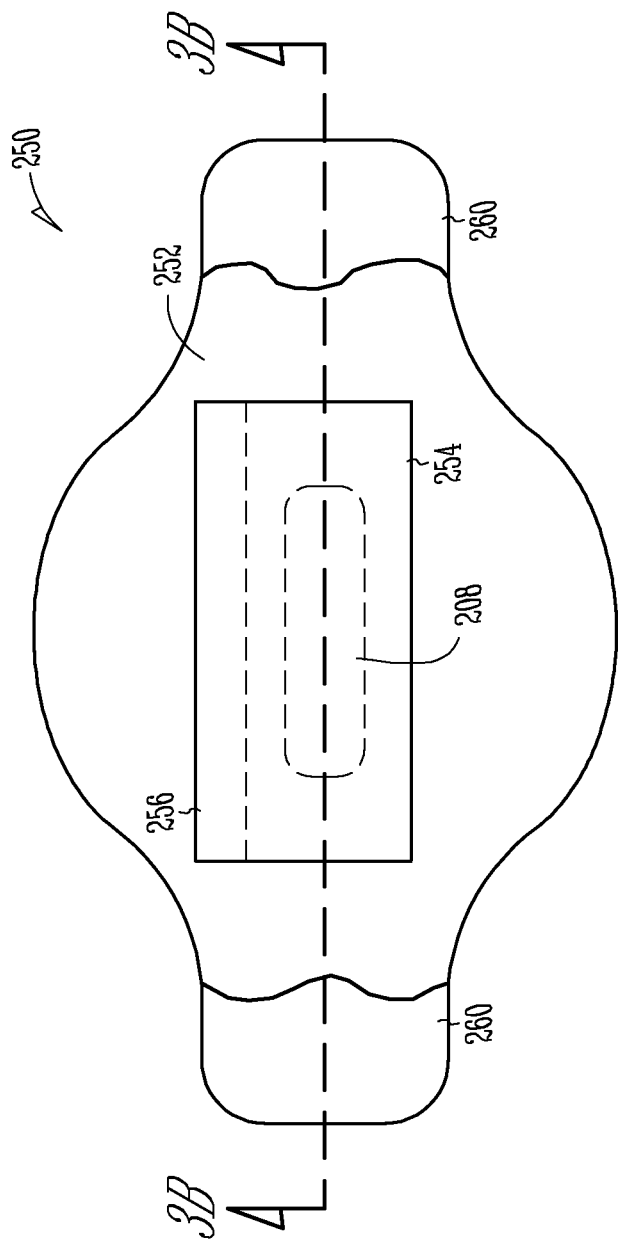
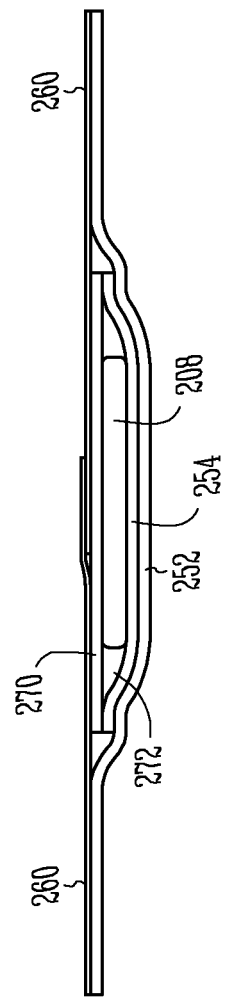

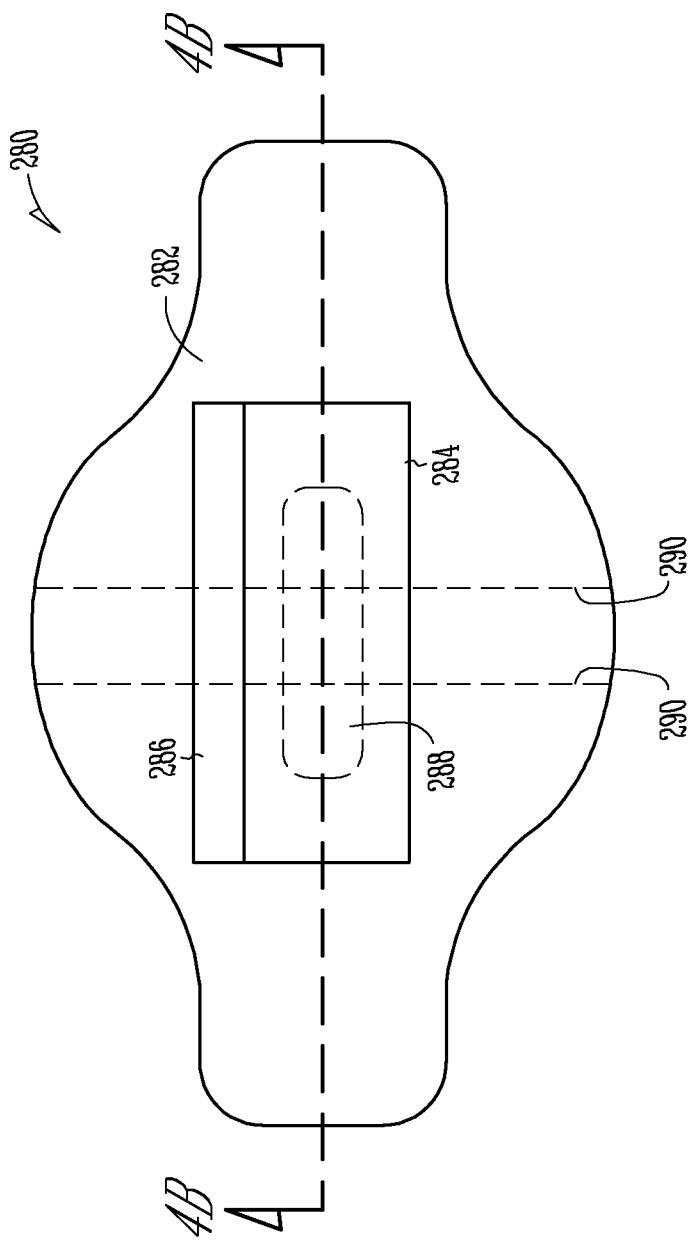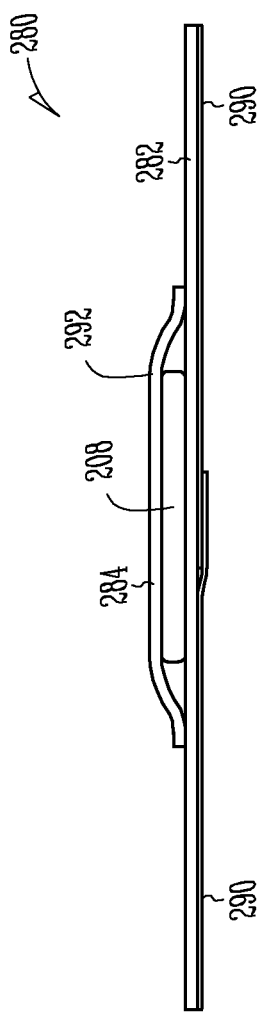

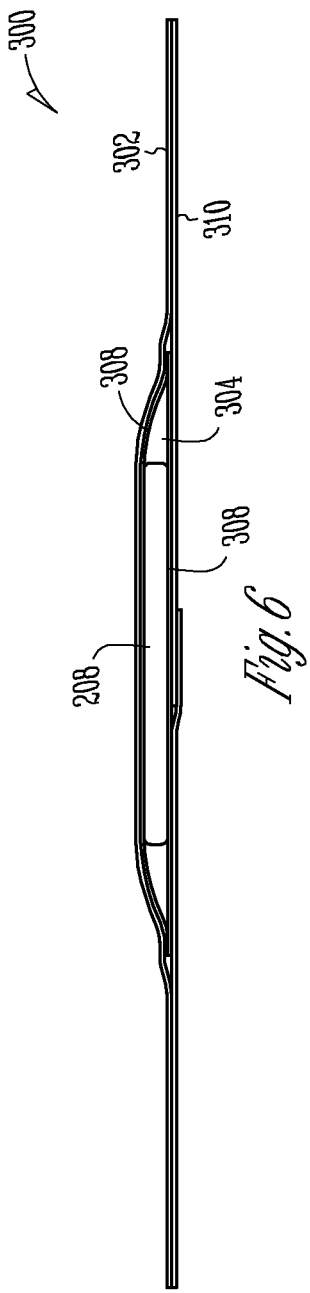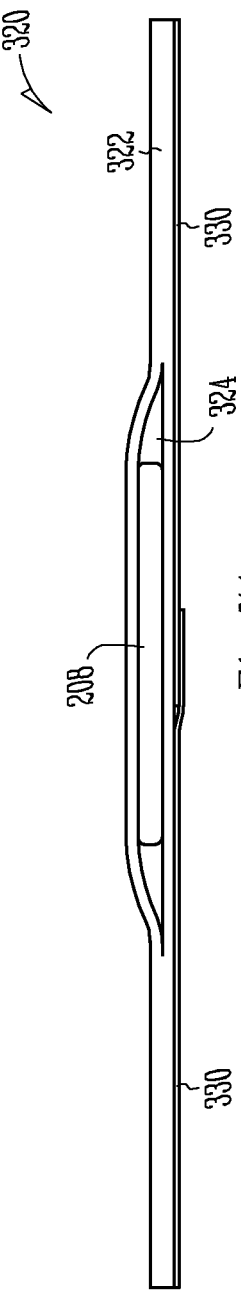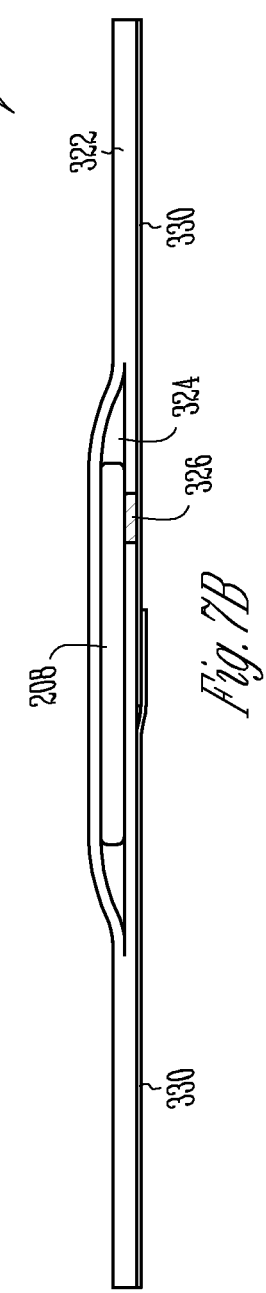

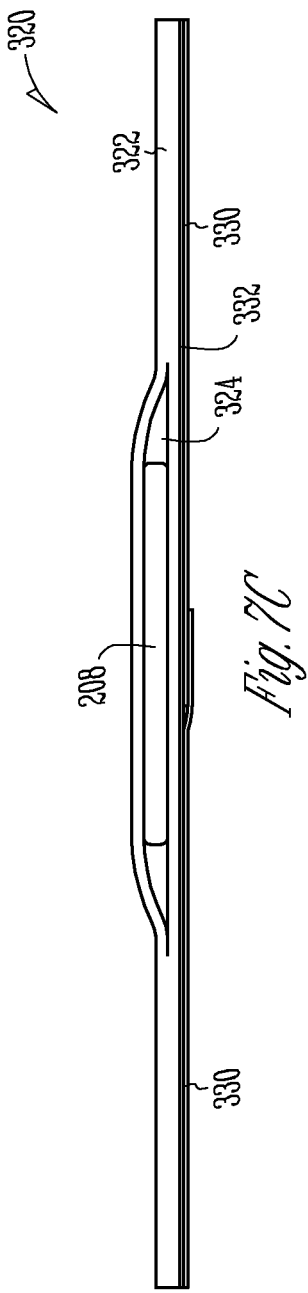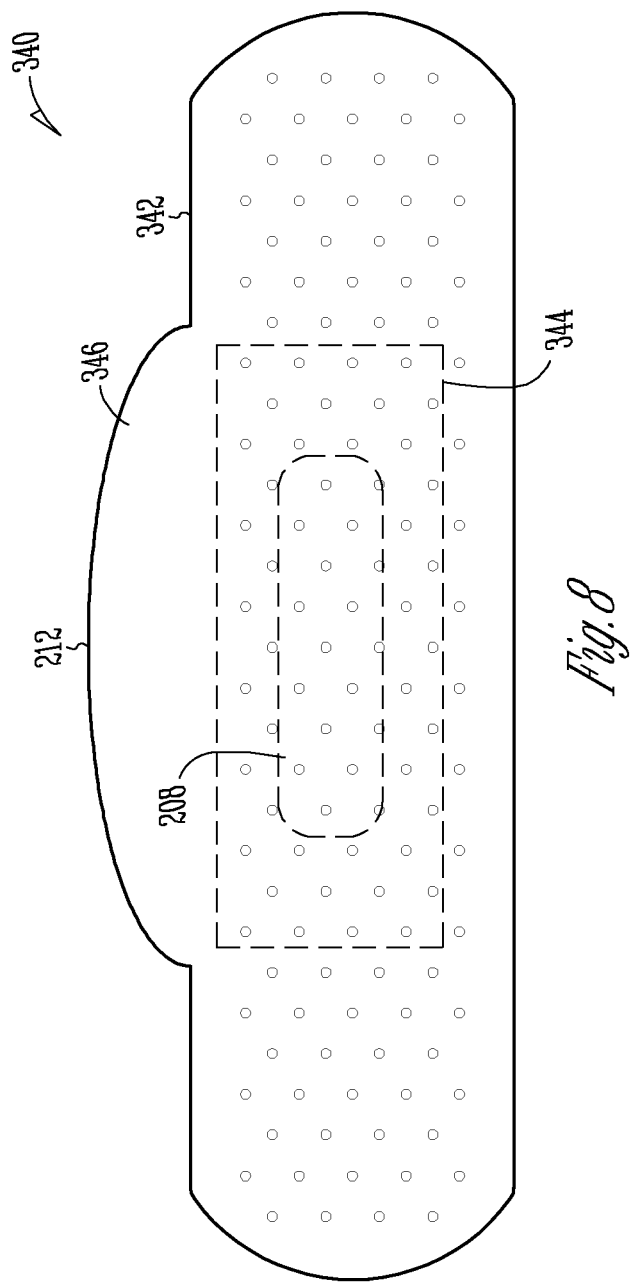

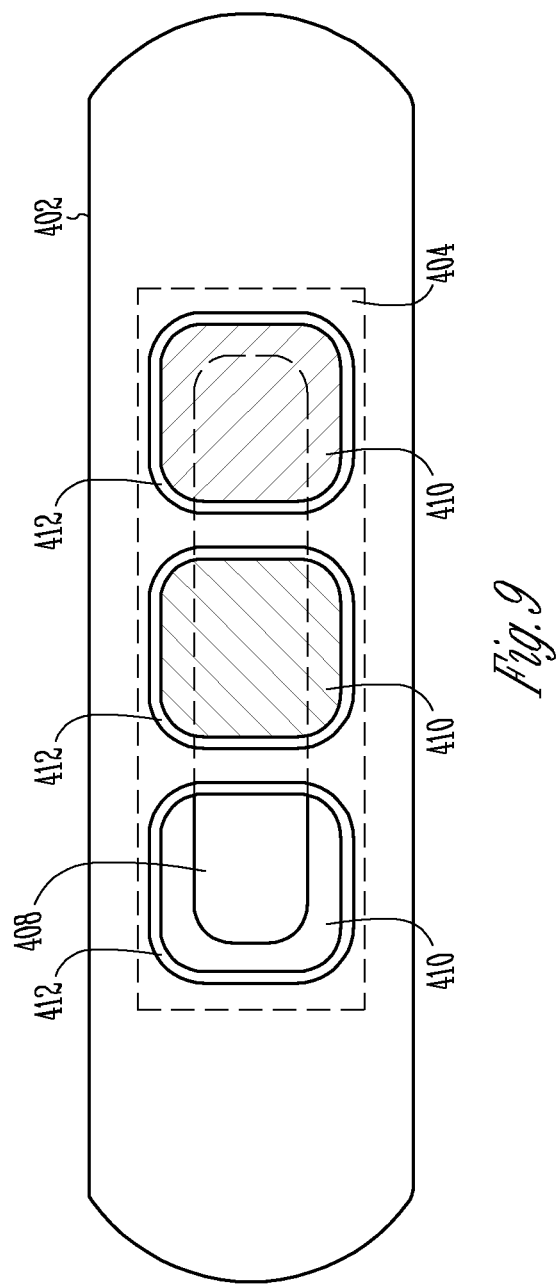

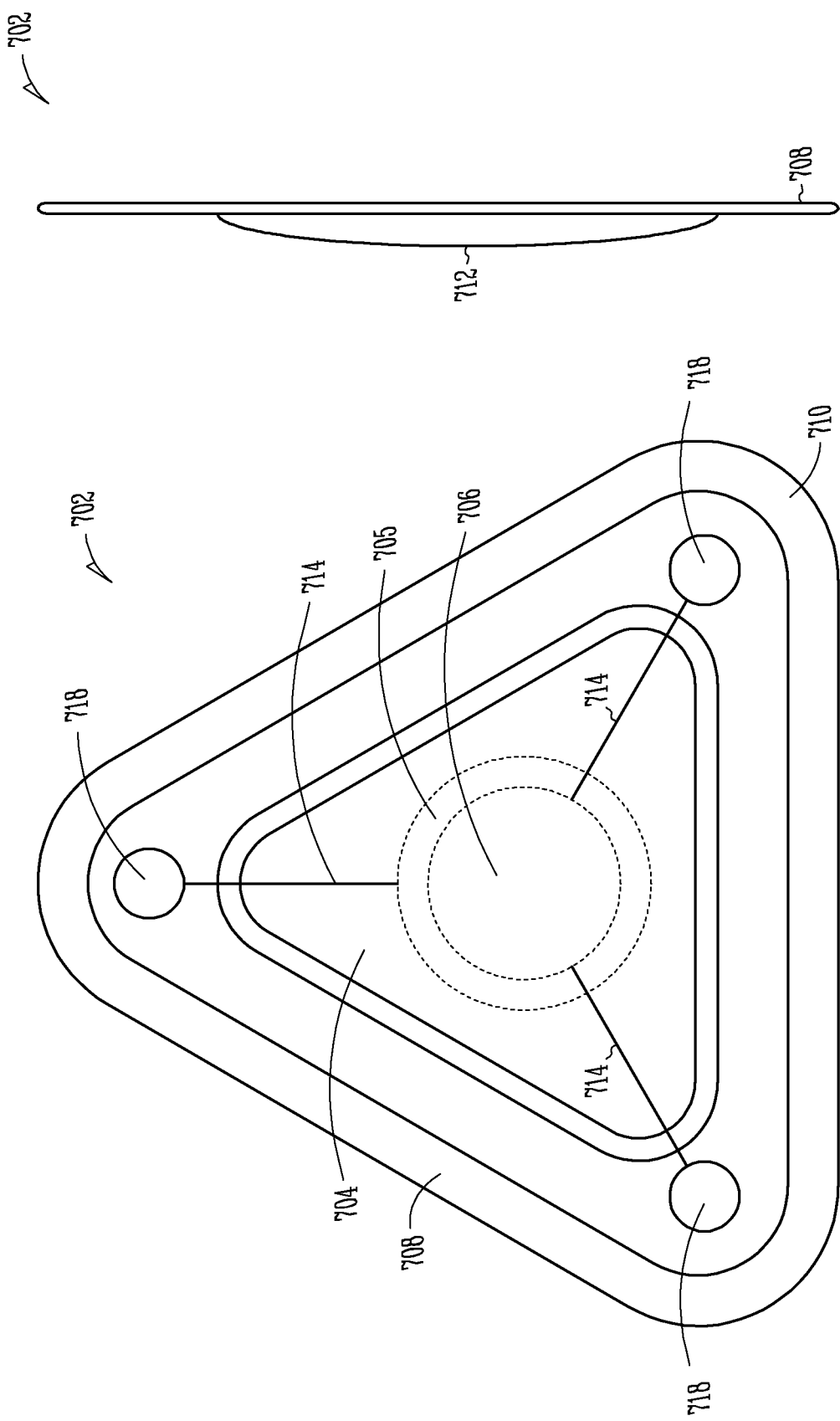

SYSTEM AND METHOD FOR PHYSIOLOGICAL MONITORING

RELATED APPLICATION

The present application claims the benefit under 35 U.S.C. 119(e) of U.S. Provisional Patent Application Ser. No. 61/385,266, filed Sep. 22, 2010, and is a Divisional of U.S. patent application Ser. No. 13/238,957, filed Sep. 21, 2011, which are incorporated herein by reference in their entirety.

BACKGROUND

Mammals display physiological states that reflect their experiences. It can be advantageous to monitor the physiological state of mammals. To date, such monitoring has been difficult and expensive.

BRIEF DESCRIPTION OF THE DRAWINGS

FIG. 2b illustrates a cross-sectional view of a sensor pocket that can be used in the sensor platform of FIG. 2a.

FIG. 3a illustrates a bottom view of another sensor platform that can be used in the system of FIG. 1.

FIG. 3b illustrates a cross-sectional view of a sensor pocket that can be used in the sensor platform of FIG. 3a.

FIG. 4a illustrates a top view of another sensor platform that can be used in the system of FIG. 1.

FIG. 4b illustrates a cross-sectional view of a sensor pocket that can be used in the sensor platform of FIG. 4a.

FIGS. 6 and 7a-7c illustrate cross-sectional views of sensor pockets that can be used in a sensor platform.

FIG. 8 illustrates a top view of another sensor platform that can be used in the system of FIG. 1.

FIGS. 9 and 10 illustrate bottom views of sensor platforms that can be used in the system of FIG. 1.

FIG. 14b illustrates a side view of the sensor platform of FIG. 15a.

FIGS. 15B-C illustrate top and side views, respectively of a sensor platform that can be used in the system of FIG. 1.

DETAILED DESCRIPTION

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

This document describes, among other things, systems, methods and apparatus for monitoring the physiology of mammals and for determining activation and recovery patterns surrounding the physical, mental and/or emotional state of the mammal as a function of the physiological data.

In one embodiment, a wireless monitoring device containing one or more sensors is attached to the subject; the sensors detect physiological attributes of the subject while the monitoring device collects the detected attributes as sensor data. The monitoring device takes the sensor data from the sensor and detects physiological events as a function of the received data. In some embodiments, sensor data from the sensor is combined with data from other sources to more fully characterize a physiological event. Contextual data surrounding the events is associated with the events and is used to develop contextual association for one or more of the events. Patterns of activation, duration, quality and recovery of the subject's physical mental or emotional state is then determined as a function of physiology and context.

Examples of contextual data may relate to: circadian, ultradian, and meridian flow cycles; quantity, quality, functionality and biochemical properties of nutritional intake and energy expenditure; quantity, timing, duration, and quality of sleep/rest patterns; strength building and resilience training activities such as exercise, meditation, biofeedback, breathing, relaxation, mindfulness and positive cognitive reframing exercises; hydration level; characterizations of external stimulation such as time, location, people and subject matter surrounding external stimuli; characteristics of internal stimulation such as memories, past experiences and learning, attitudes, beliefs and perceptions, patterns of rewards and punishments; and levels of biochemical messengers such as serotonin, endorphins, cortisol, epinephrine, norepinephrine, GABA, insulin, glucose, DHEA, leptin, ghrelin and dopamine. Contextual information may also include underlying medical conditions, genomic and proteomic information, risk factors and family history.

In one example application, the sensor measures physiological activity of a subject patient for an extended period of time. Sensor data is collected and analyzed to quantify and characterize the physiological patterns of the subject's mental, emotional and physical processing of daily events and activities.

Figure 1:
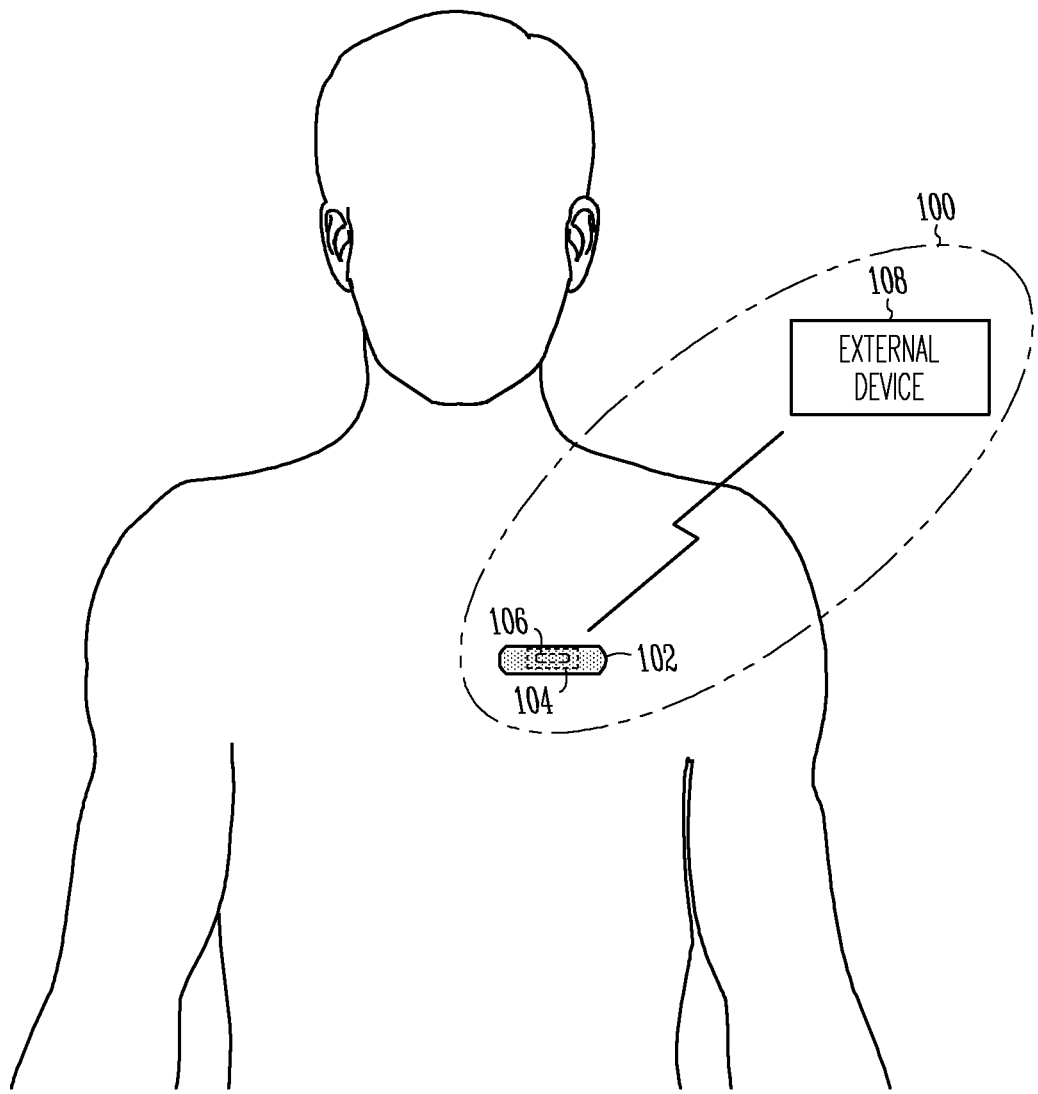
FIG. 1 illustrates an example of a system for physiological monitoring, according to various embodiments of the invention.

FIG. 1 illustrates an example of a physiological monitoring system 100. Monitoring system 100 includes a sensor platform 102 and a monitor unit 106. In the embodiment shown in FIG. 1, sensor platform 102 includes a pocket 104 into which is inserted a sensor module 106. In one example embodiment, sensor module 106 communicates with external device 108 via a wireless communication protocol. Other communication protocols can be used as well. For example, in one embodiment, sensor module has a communications interface that includes a computer interface. The computer interface is used to connect sensor module 106 to a computer for communication. A communications interface that is a combination of wireless and physical interface is especially well suited for long range monitoring of a subject.

In one embodiment, external device 108 includes a monitoring system which processes sensor data transmitted or read from sensor platform 102. In another embodiment, sensor module 106 includes a monitoring unit and one or more sensors. In one such embodiment, the monitoring unit of sensor module 106 processes the data from the sensors in order to detect particular physiological conditions and communicates data corresponding to the detected physiological conditions to external device 108 for display.

In one example embodiment, sensor module 106 is implanted subcutaneously in the patient being studied. In another example embodiment, sensor module 106 is inserted or installed in a sensor platform (such as sensor platform 102) that is attached to the patient. The point of attachment could be an appendage such as an arm, leg or finger, an earlobe, or a location on the body such as a hip, the skin, the inside of the mouth, etc. In one such embodiment, sensor module 106 is imbedded in or surrounded by a conductive gel within the sensor platform; the conductive gel increases conductivity between an electrical sensor and the subject's skin. In another embodiment, sensor module 106 rests on top of the conductive gel.

In one example, sensor module 106 exports raw data and the data is captured and processed by monitor unit 108. In another embodiment, physiological data is captured and stored by sensor module 106, compressed and transmitted to external device 108 periodically. In yet another embodiment, physiological data is captured by the sensor or sensors within sensor module 106, and that data is processed, analyzed and stored by a monitoring unit within sensor module 106. In one embodiment, external device 108 is an applet running on a computer or smart phone. In another embodiment, external device 108 is an application running on a physician monitor or home base station. For instance, the applet or application could display the results of the processing by the monitoring unit in sensor module 106, or could be used to control and/or change the operation of the monitoring unit in sensor module 106.

In one approach, the applet or application processes raw data or processed data received from sensor module 106. Such and approach can reduce the computing requirements of sensor module 106.

In one example embodiment, sensor module 106 is an implantable cardiac monitor such as the Reveal® DX Insertable Cardiac Monitor manufactured by Medtronic or the St. Jude Confirm™ Implantable Cardiac Monitor manufactured by St. Jude Medical. In another example embodiment, sensor module 106 is a Reveal® XT Insertable Cardiac Monitors, also manufactured by Medtronic. Each of these devices can be used for long-term monitoring of subjects for heart rate activity and heart rate variability (HRV). In one example embodiment, sensor module 106 is an implantable loop monitor.

In one example embodiment, sensor module 106 is a field programmable device such as a field programmable gate array (FPGA). In one such embodiment, a portion of the FPGA is programmed to implement some or all of the functions of a cardiac monitor. In another such embodiment, a portion of the FPGA is programmed to implement some or all of the functions of a loop monitor.

In one embodiment, sensor module 106 includes an interface that allows sensor module 106 to be reprogrammed. In one such embodiment, external device 108 reprograms sensor module 106 via its FPGA interface to add or improve functionality. In one example, external device 108 programs the underlying FPGA to add a monitoring unit to sensor module 106. In one example embodiment, the monitoring unit receives the raw data from the cardiac monitor or loop monitor and processes it to detect events of interest before forwarding the data to external device 108.

In one embodiment, sensor module 106 includes a sensor module (e.g., a cardiac monitor or a loop monitor) and a monitoring unit. A device such as a cardiac monitor may require approval from the Food and Drug Administration (FDA), while a monitoring unit might not need such approval. In one embodiment, external device 108 includes software which prevents modification of the approved cardiac portion of the FPGA, while permitting changes to the other sections of the FPGA. In another embodiment, external device 108 includes software which restricts modification of the approved cardiac portion of the FPGA to approved personnel (e.g., to correct errors in the implemented cardiac monitor), while permitting changes to the other sections of the FPGA. In either embodiment, it can be advantageous to limit changes to the cardiac monitor while permitting addition to or improvement of of the sensor module 106 in general. Such an approach can be used, for instance, to port existing monitoring programs to sensor module 106.

Figure 2A:
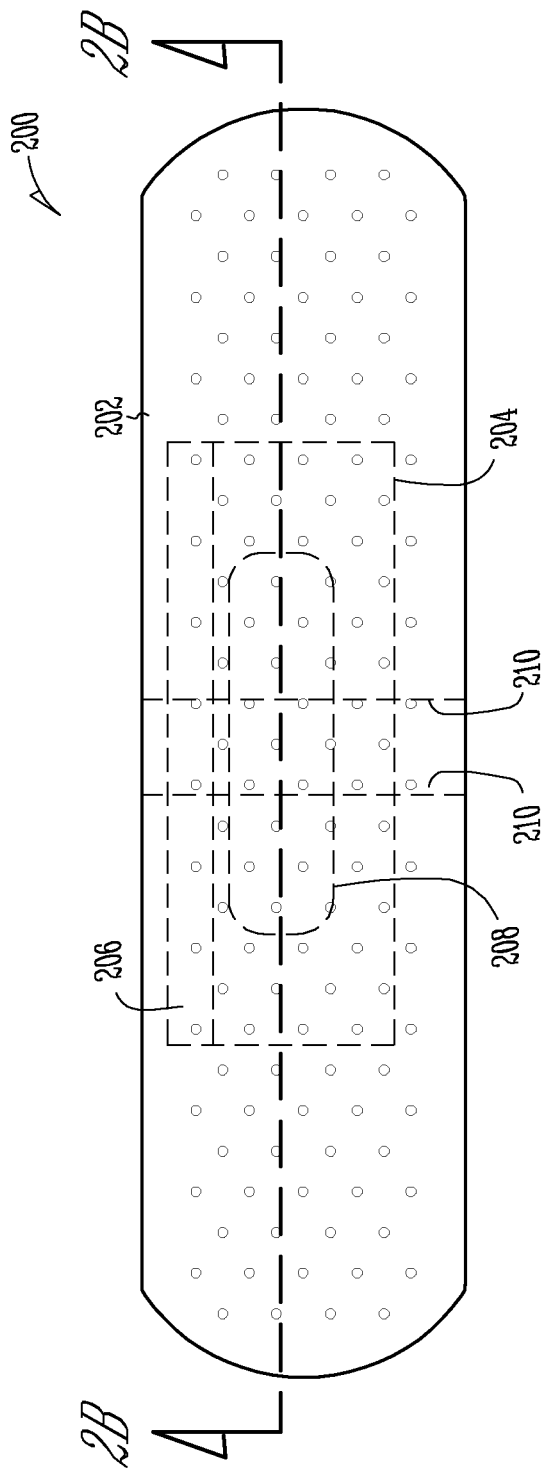
FIG. 2a illustrates a top view of one sensor platform that can be used in the system of FIG. 1.

FIG. 2*a* illustrates a top view of one sensor platform that can be used in the system of FIG. 1. In the example shown in FIG. 2*a*, sensor platform 200 includes a tape strip 202 and a sensor pocket 204. Tape strip 202 includes an adhesive used to secure the platform to the body of the subject.

Sensor pocket 204 includes a section 206 that can be used to close pocket 204 after a sensor module is inserted. A user inserts a wireless sensor module 208 into pocket 204 and secures the sensor in pocket 204 via section 206. Release sheets 210 protect tape strip 202 and the exposed side of sensor pocket 204 and are removed from the strip ends of tape strip 202 at the time of use in order to expose the adhesive and permit placement of the sensor platform on the subject. In one example approach, tape strip 202, section 206 and pocket 204 are constructed such that, when assembled, they protect the sensor module from the external environment while allowing the enclosed sensor module to detect the requisite physiological attributes of the subject. In one embodiment, sensor module 208 could be any of the monitors discussed for sensor module 106 above.

In one example, section 206 includes a surface protected by one or more release sheets. The surface is exposed by removing the release sheets. The surface is then pressed against the adhesive surface of tape strip 202 to seal sensor pocket 204.

In one approach tape strip 202 includes a backing material made with hydrophobic polyurethane foam. One advantage of polyurethane foam is that it permits water vapor to escape from the surface of the skin, but keeps liquid water from reaching the surface of the skin. Other backing materials, such as fabric, polyethylene or polyvinyl chloride could be used as well.

It can be advantageous to use a material that is flexible in multiple directions since bunching of the backing material can add to the background noise. One such material is used in the Band-Aid® Activ-Flex™ bandage.

Figure 2B:
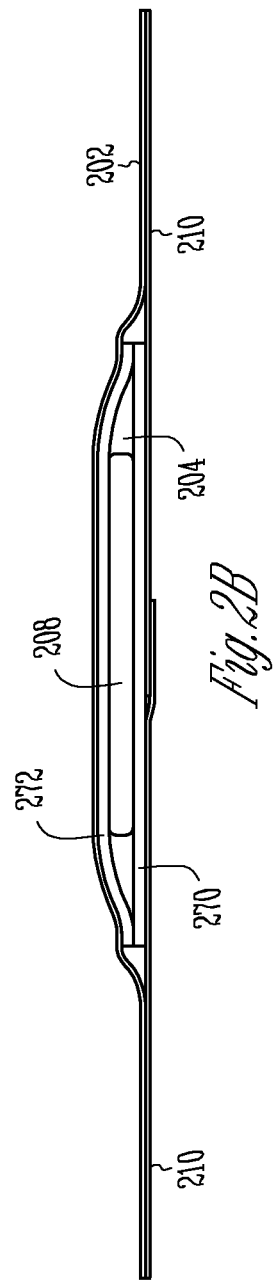

FIG. 2b illustrates a cross-sectional view along the 2b-2b axis of pocket 204, tape strip 202 and sensor module 208 in one example of sensor platform 200 of FIG. 2a.

As can be seen in FIG. 2b, in one example approach pocket 204 includes a first layer 270 and a second layer 272. In use, layer 270 is pressed against a surface of the test subject, while layer 272 is attached to the adhesive side of tape strip 202.

The material used for layer 270 may be a function of the type of sensor being used. Sensor module 208 may monitor a number of physiological parameters. For instance, in one example approach, sensor module 208 monitors heart sounds. In such an approach, layer 270 could be chosen to transfer acoustic signals such as heart sounds effectively, while layer 272 could be chosen to isolate sensor module 208 from environmental noise and motion artifact to the extent desired.

In another example approach, sensor module 208 monitors electrical signals representative of heart function. In such an approach, layer 270 could be chosen to transfer electrical signals effectively, while layer 272 could be chosen to isolate sensor module 208 from environmental signal artifacts to the extent desired.

In yet another example approach, sensor module 208 monitors motion or activity of an individual. In one such approach layer 270 is chosen based on properties that allow it to conform to the body while layer 272 is chosen to hold the sensor module securely against the body to mitigate undesired signal artifacts.

In one approach, layer 270 is a thin plastic-like film that separates the sensor module from the subject's skin for sterility purposes yet does not prohibit or significantly impede transcutaneous signal acquisition between the sensor module and the skin. In another embodiment, layer 270 is a hydrocolloid layer treated to enhance electrical conductivity. In yet another approach, layer 270 is formed from a hydrogel.

In some embodiments, layer 270 includes an adhesive.

In some example embodiments, layer 272 could be chosen to provide some degree of protection from bumps or from static electricity for sensor module 208.

In one approach, sensor pocket 204 is manufactured. Pocket 204 is then attached to tape strip 202 by, e.g., an adhesive applied to layer 272. Section 206 is folded back over layer 270. Release sheets 210 are then added to protect layer 270 and the adhesive side of tape strip 202.

To use, a user removes release sheets 210, opens pocket 204 and inserts sensor module 208. The user then presses section 206 against the adhesive of tape strip 202 to close pocket 204.

In one example embodiment, tape strip 202 is not adhesive in the area where the sensor module 208 resides. In such an embodiment, sensor platform 200 can be manufactured without a layer 272.

FIG. 3a illustrates a top view of a sensor platform 250 that can be used in the system of FIG. 1. In the example shown in FIG. 3a, sensor platform 250 includes a tape strip 252 and a sensor pocket 254. In one example embodiment, tape strip 252 is a hydrocolloid with adhesive properties, such as the Activ Flex® brand of products produced by Johnson & Johnson. In another example embodiment, tape strip 252 is a hydrogel that can be attached to the subject being monitored.

In the example shown in FIG. 3a, sensor pocket 254 includes a section 256 that can be used to seal pocket 254 after a sensor module is inserted. The user inserts a wireless sensor module 208 into pocket 254 and secures the sensor module in pocket 254 via section 256. Release sheets 260 protect tape strip 252 and the exposed side of sensor pocket 254 and are removed from the strip ends of tape strip 252 at the time of use in order to expose the hydrocolloid surface of tape strip 252 and permit placement of the sensor platform on the subject. In one example approach, tape strip 252, section 256 and pocket 254 are constructed such that, when assembled, they protect the sensor module from the external environment while allowing the enclosed sensor module to detect the requisite physiological attributes of the subject. For instance, in some embodiments tape strip 252 is constructed from hydrophobic acoustic foam, or similar materials, in order to reduce the impact of ambient noise.

In one example embodiment, tape strip 252 includes an adhesive disposed on the patient facing surface to enhance adhesion.

FIG. 3b illustrates a cross-sectional view along the 3b-3b axis of pocket 254, tape strip 252 and sensor module 208 in one example of sensor platform 250 of FIG. 3a. As can be seen in FIG. 3b, pocket 254 includes a first layer 270 and a second layer 272. In use, layer 270 is pressed against a surface of the test subject, while layer 272 is attached to the adhesive side of tape strip 252. As was discussed with regard to FIGS. 2a and 2b above, layers 270 and 272 can be selected based on the physiological parameters being measured by sensor module 208.

In one example, section 256 includes a surface protected by one or more release sheets. The surface is exposed by removing the release sheets. The surface is then pressed against the surface of tape strip 252 to close or seal sensor pocket 254.

In another embodiment, section 256 is folded back over layer 270 and protected by release sheets 260. Section 256 is exposed by removing the release sheets 260. The surface is then pressed against the surface of tape strip 252 to seal sensor pocket 254.

In one embodiment, sensor platform 250 provides an external environment replicating a subcutaneous implant environment while removing the risks (e.g., infection and scarring) of implanting and then removing an implantable device. In another embodiment, sensor platform 250 provides one or more properties of the subcutaneous environment chosen to enhance the performance of sensor module 208. Some such properties include electrical conductivity, sound deadening, and reduction in motion artifacts. Such approaches also provide access to more sophisticated implant technology while removing the risks of implantation and explantation. This approach is also advantageous to implantable medical device manufacturers. By creating a non-invasive means to leverage implantable technology without significantly modifying the design or manufacturing process, it allows a product offering for situations where shorter or more periodic monitoring may be more appropriate prior to committing to an implantable medical device.

In the example shown in FIG. 3a, sensor platform 250 includes a flexible tape strip 252 with an integral sensor pocket 254. In one such embodiment, the sensor pocket receives a subcutaneous implant and includes a hydrogel adhesive used to attach the sensor pocket to the skin of a patient. In one example embodiment, the implant is immersed in a conductive gel used to increase conductivity between the implant and the subject's skin. In another such embodiment, the sensor pocket is a hydrogel or hydrocolloid material. In some such embodiments, the sensor pocket material is modified to enhance transmission of the physiological parameters being measured.

FIG. 4a illustrates a top view of a sensor platform 280 that can be used in the system of FIG. 1. In the example shown in FIG. 4a, sensor platform 280 includes a tape strip 282 and a sensor pocket 284. In one approach, tape strip 282 is a hydrocolloid formed by disposing an absorbent layer of gel on semi-permeable film or foam. In another, tape strip 282 is hydrogel. The hydrocolloid and hydrogel approaches can be manufactured to enhance, for example, electrical connectivity.

In the example shown in FIG. 4a, sensor pocket 284 includes a section 286 that can be used to close pocket 284 after a sensor module is inserted. In the example shown, pocket 284 is mounted to the top side of tape strip 202.

As before, the user inserts a wireless sensor module 208 into pocket 284 and secures the sensor module in pocket 284 via section 286. Release sheets 290 protect tape strip 282 and are removed from the strip ends of tape strip 282 at the time of use in order to expose the surface of tape strip 282 and permit placement of the sensor platform on the patient. In one example approach, tape strip 282, section 286 and pocket 284 are constructed such that, when assembled, they protect the sensor module from the external environment while allowing the enclosed sensor module to detect the requisite physiological attributes of the patient.

In one example embodiment, tape strip 282 includes an adhesive disposed on the patient facing surface to enhance adhesion.

In one example, section 286 includes a surface protected by one or more release sheets. The surface is exposed by removing the release sheets. The surface is then pressed against the surface of tape strip 282 to seal sensor pocket 284.

FIG. 4b illustrates a cross-sectional view along the 4b-4b axis of pocket 284, tape strip 282 and sensor module 208 in one example of sensor platform 280 of FIG. 4a. As can be seen in FIG. 4b, pocket 284 includes a single layer 292 attached to the back-side of tape strip 282. In use, the adhesive side of tape strip 283 is pressed against a surface of the test subject, while layer 292 is attached to the other side of tape strip 282.

In one example, section 286 includes a surface protected by one or more release sheets. The surface is exposed by removing the release sheets. The surface is then pressed against the surface of tape strip 282 to seal sensor pocket 284

In one example embodiment, tape strip 282 is formed from a hydrogel or hydrocolloid material. In one such embodiment, layer 292 is formed from hydrogel. In another such embodiment, layer 292 is formed from a hydrocolloid material.

In one embodiment, tape strip 282 is formed from polyurethane foam. Other backing materials, such as fabric, polyethylene or polyvinyl chloride could be used as well. In some such embodiments, tape strip 282 includes a thin film window against which layer 292 is attached. Sensor module 208 senses its physiological parameters through the thin film.

Figure 5:
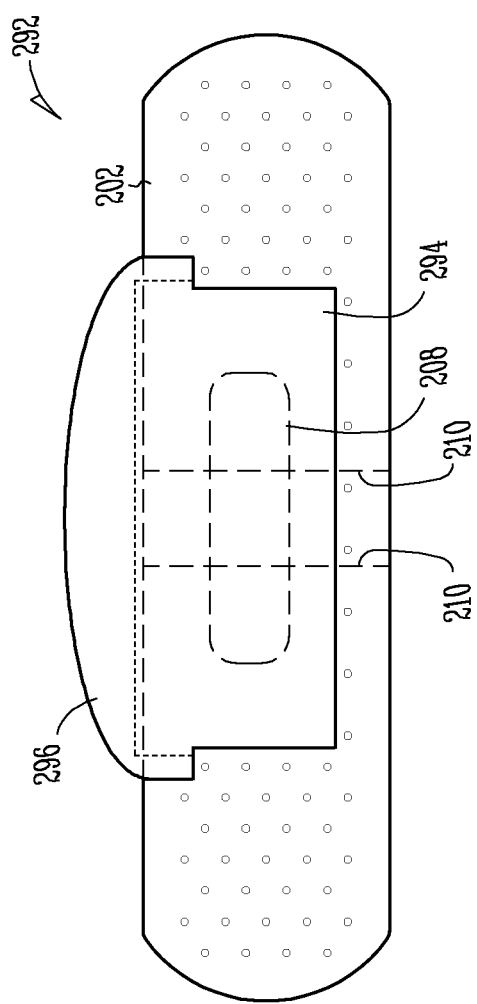
FIG. 5 illustrates a top view of another sensor platform that can be used in the system of FIG. 1.

FIG. 5 illustrates a top view of another sensor platform that can be used in the system of FIG. 1. In the example shown in FIG. 5, sensor platform 292 includes a tape strip 202 and a sensor pocket 294. Tape strip 202 includes an adhesive used to secure the platform to the body of the subject.

Sensor pocket 294 is attached to the non-adhesive side of tape strip 202 and includes a section 296 that can be used to close pocket 294 after a sensor module is inserted. A user inserts a wireless sensor module 208 into pocket 294 and secures the sensor in pocket 294 by pressing the adhesive side of section 296 against a patient's skin.

In one example approach, section 296 includes an adhesive surface on the area outside the dotted line (sealing the pocket to the top of strip 202 and onto the patient's skin. In one such embodiment, release sheets 210 protect tape strip 292 and the adhesive side of section 296; the release sheets are removed from the strip ends of tape strip 202 and the adhesive side of section 296 at the time of use in order to expose the adhesive and permit placement of the sensor platform on the patient. In one example approach, tape strip 202, section 296 and pocket 294 are constructed such that, when assembled, they protect the sensor module from the external environment while allowing the enclosed sensor module to detect the requisite physiological attributes of the patient.

In one approach tape strip 202 includes a backing material made with hydrophobic polyurethane foam. One advantage of polyurethane foam is that it permits water vapor to escape from the surface of the skin, but keeps liquid water from reaching the surface of the skin. Other backing materials, such as fabric, polyethylene or polyvinyl chloride could be used as well.

FIG. 6 illustrates a cross-sectional view of a sensor platform 300. In one embodiment, such as is shown in FIG. 6, sensor platform 300 includes a tape strip 302 with a sensor pocket 304. In the embodiment shown, pocket 304 is formed by attaching one or more thin film panels 308 to the adhesive side of tape strip 302. In one example embodiment, tape strip 302 is formed from polyurethane foam. Other backing materials, such as fabric, polyethylene or polyvinyl chloride could be used as well. Sensor module 208 senses its physiological parameters through the thin film.

Release sheets 310 protect tape strip 302 and the skin side of sensor pocket 304 and are removed from the strip ends of tape strip 302 at the time of use in order to expose the skin side of pocket 304 and the surface of tape strip 302 and permit placement of the sensor platform on the patient. In one example approach, tape strip 302 and pocket 304 are constructed such that, when assembled, they protect the sensor module from the external environment while allowing the enclosed sensor module to detect the requisite physiological attributes of the patient.

In one embodiment, such as is shown in FIG. 7a, sensor platform 320 includes a tape strip 322 with a sensor pocket 324 formed in tape strip 322. Release sheets 330 protecting tape strip 322 are removed from tape strip 322 at the time of use in order to expose the surface of tape strip 322 and permit placement of the sensor platform on the patient. In one approach, a hydrocolloid material is used for tape strip 322. In another approach a hydrogel material is used for tape strip 322. Other materials could be used as needed. In one example approach, tape strip 322 and pocket 324 are constructed such that, when assembled, they protect the sensor module from the external environment while allowing the enclosed sensor module to detect the requisite physiological attributes of the patient.

In one example embodiment, such as is shown in FIG. 7b, tape strip 322 includes one or more sensor windows 326. In one embodiment, sensor window 326 is a hydrogel in a hydrocolloid tape strip 322. In another embodiment, sensor window 326 is electrically conductive while the rest of tape strip 322 is less electrically conductive or is an insulator. In another embodiment, sensor window 326 is thin film. In yet another embodiment, sensor window 326 is open to provide direct skin contact for sensor module 208.

In one example embodiment, such as is shown in FIG. 7c, tape strip 322 includes an adhesive film 332 disposed on the patient facing surface to enhance adhesion.

FIG. 8 illustrates a top view of another sensor platform that can be used in the system of FIG. 1. In the example shown in FIG. 8, sensor platform 200 includes a tape strip 342 and a sensor pocket 344. Tape strip 342 includes an adhesive used to secure the platform to the body of the subject. Tape strip 342 also includes a section 346 that can be folded over the open end of pocket 344 in order to close the pocket 344. In one such embodiment, the same adhesive is used on section 346 as is used on the rest of tape strip 342.

FIG. 9 illustrates a skin-side view of a tape strip 402 with a sensor pocket 404 attached to its opposite side. Pocket 404 is constructed to receive a sensor module 408 having more than one physiological monitoring sensor. In the example shown, three or more sensors are integrated into the one sensor module 408.

In the example shown in FIG. 9, a window 410 is provided in tape strip 402 for each sensor. In one such embodiment, gaskets 412 provide some degree of environmental isolation between sensors in sensor module 408. In one embodiment, windows 410 include a material used to provide protection (such as a thin film) or a material used to enhance transmissivity of the parameter being measured. For instance, one of the windows 410 might include a hydrogel used to enhance electrical conductivity.

In one approach, two or more sensors are used to capture physiological data. In one such approach, one of the sensors measures ECG, heart rate and Heart Rate Variability (HRV) indicative of Autonomous Nervous System activity. The other sensor measures a parameter such as cortisol level or glucose level.

In one embodiment, cortisol in the blood is measured via a blood test. The cortisol measurement is then correlated with the physiological measurements to more accurately map the effects of stress.

In one such approach, cortisol is measured periodically by the user and the measurement is entered into external device 108. In one such approach, a cortisol meter (similar to a glucose meter) measures cortisol in the blood extracted from a finger prick. In another approach, the cortisol meter measures cortisol levels in saliva. In yet another approach, a continuous cortisol sensor is worn by the user similar to a continuous glucose sensor with wireless transmission of the sensor data transmitted to a monitoring device such as the sensor module described here. In yet another approach, a glucose meter measures both cortisol and blood glucose. Such a meter can be effective in monitoring and changing behavior in people with diabetes.

Other sensors can be used as desired in the sensor platform of FIG. 9, including electrical, chemical or mechanical sensors, clocks, GPS, telemetry, or sensors incorporated in other units (such as the cortisol or insulin meters above).

Figure 10:
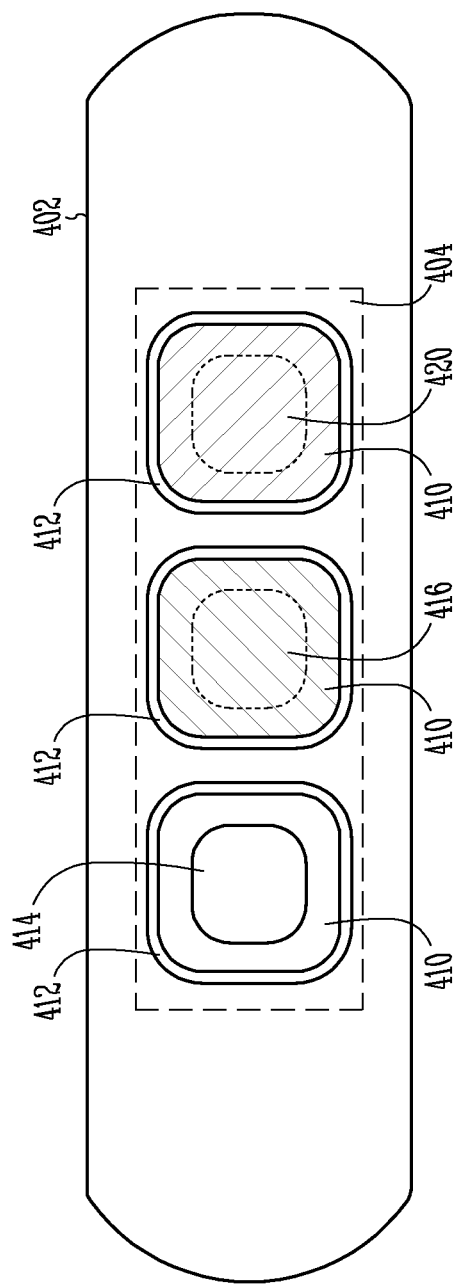

FIG. 10 illustrates a skin-side view of a tape strip 402 with a sensor pocket 404 attached to its opposite side. In the example shown, pocket 404 is constructed to receive sensor modules 414, 416 and 418. In the example shown, a window 410 is provided in tape strip 402 for each sensor. In one such embodiment, gaskets 412 provide some degree of environmental isolation between sensors in sensor module 408. In one embodiment, windows 410 include a material used to provide protection (such as a thin film) or a material used to enhance transmissivity of the parameter being measured. For instance, one of the windows 410 might include a hydrogel used to enhance electrical conductivity.

In one embodiment, a sensor includes an electrode that, when assembled, passes through one or more windows 410 to make direct contact with the patient's skin.

In one embodiment, sensor module 414 includes a monitoring unit that receives data from each of sensor modules 414, 416 and 420 and processes that data to detect physiological events as a function of the sensor data. The monitoring unit also receives sensor data from other sensors that are exterior to sensor platform 402 and correlates the external sensor data with sensor data from sensor module 414, 416 and 420 to establish context surrounding the physiological events. The monitoring unit then characterizes the activation, duration, quality and/or recovery of one or more of the patient's physical, mental and emotional states as a function of physiology and context.

In one example embodiment, sensor modules 414, 416 and 420 are wired together during the assembly of sensor module 402. In another embodiment, sensor modules 414, 416 and 420 communicate using a wireless protocol. In one such embodiment, the same wireless protocol is used to communicate with the external sensors.

In one example embodiment, external devices coupled to a patient (e.g., an insulin pump, nerve stimulator or blood pressure cuff) communicate data to a monitoring unit within sensor module 414. In other example embodiments, an implanted device such as a drug pump or a nerve stimulator communicates with the monitoring unit of sensor module 414. In one nerve stimulator embodiment, a vagal nerve stimulator is communicatively coupled to sensor module 414, and responds to sensor module 414 to stimulate the vagus nerve at the appropriate times.

In one example embodiment, a user can query the monitoring unit when desired to obtain information or status. For instance, the user can prompt the monitoring unit to capture data corresponding to a user-detected physiological event for later analysis. A user could also trigger event recording prior to engaging in a particular activity or activities.

In yet another example embodiment, a user is queried on external device 108 when the monitoring unit detects a physiological event. The query may be a text message, for instance, on a smart phone. The user can then enter data detailing what happened to cause the event.

Each of the above examples provides scenarios that allow the monitoring unit not only to identify a physiological event such as a spike in stress, but also to correlate the event with what might be the underlying cause.

Figure 11:
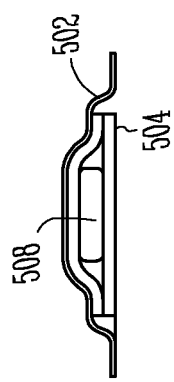
FIG. 11 illustrates cross-sectional views of a sensor pocket that can be used in a sensor platform.

FIG. 11 illustrates a cross-sectional view of a tape strip 502 with a sensor pocket 504 attached to its patient side. This cross-sectional view is orthogonal to the view in FIGS. 2b and 3b. In the example shown, pocket 504 is constructed to receive a sensor module 408 inserted from the longer axis of tape strip 402. In one such embodiment, sensor pocket 504 is formed from two strips of hydrocolloid material. In another such embodiment, sensor pocket 504 is formed from one or more strips of hydrogel material. Other materials could be used as described above, such as aloe vera or other similar materials.

Figure 12:
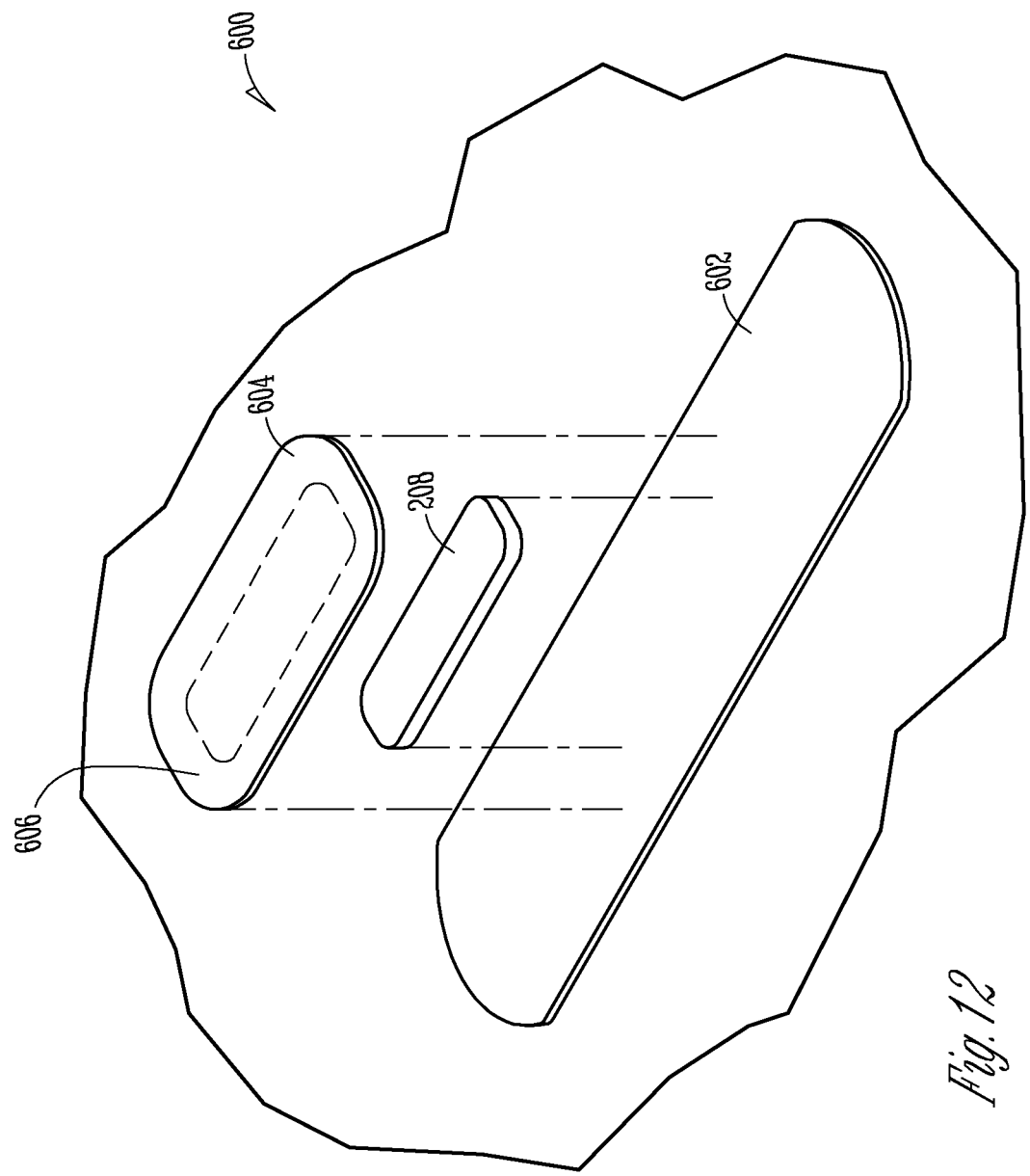
FIG. 12 illustrates an exploded view of another sensor platform that can be used in the system of FIG. 1.

FIG. 12 illustrates an exploded view of a sensor platform 600. Sensor platform 600 includes a tape strip 602, a sensor module 208 and a pocket cover 604. Pocket cover 604 includes an adhesive section 606 (outside the hashed lines on the sensor module side of pocket cover 604) used to form a pocket around sensor module 208.

Figure 13:
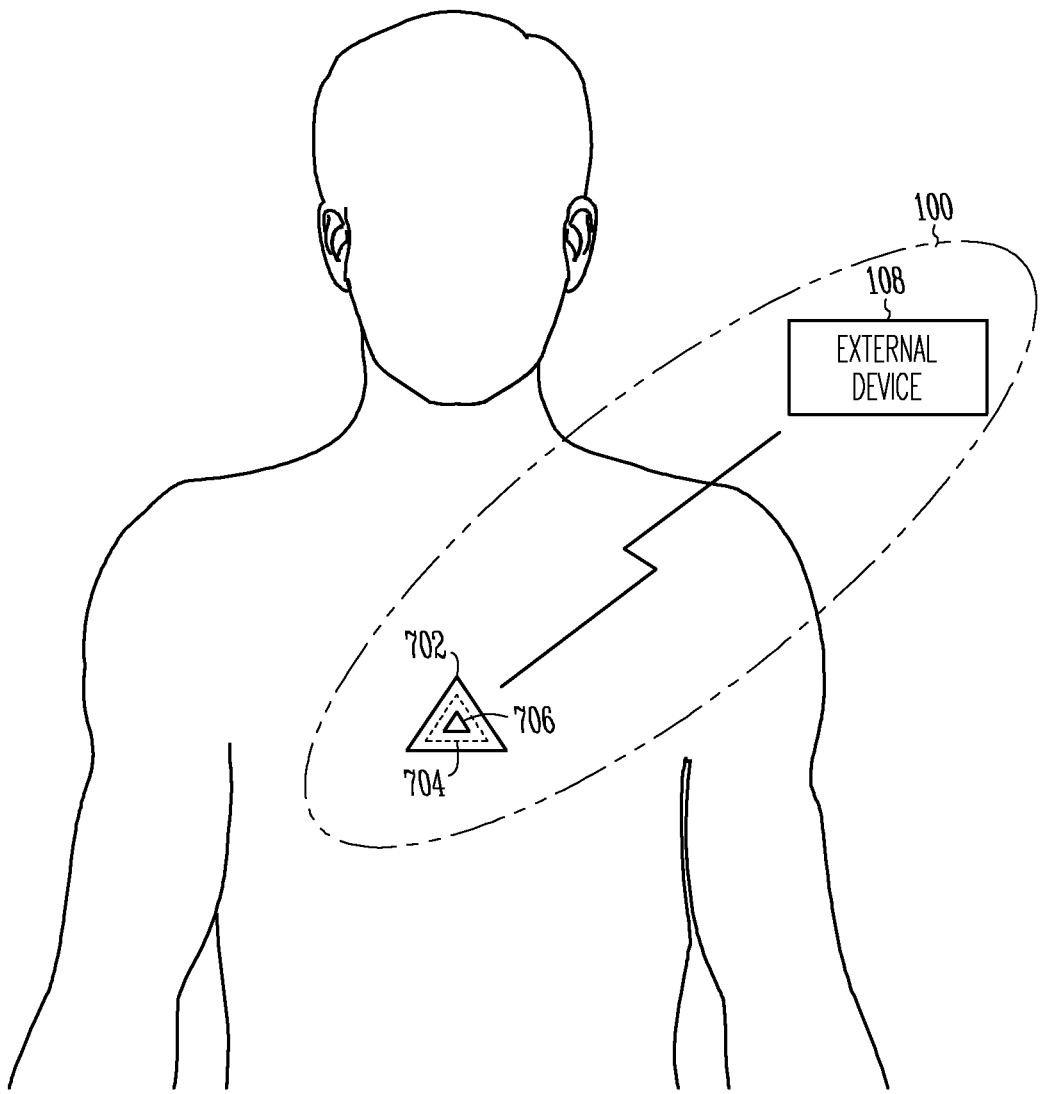
FIG. 13 illustrates another example of a system for physiological monitoring, according to various embodiments of the invention.

FIG. 13 illustrates another example of a physiological monitoring system 100. Monitoring system 100 includes a sensor platform 702 and a monitor unit 706. In the embodiment shown in FIG. 13, sensor platform 702 includes a pocket 704 into which is inserted a sensor module 706. In one example embodiment, sensor module 706 communicates with external device 108 via a wireless communication protocol.

In one embodiment, external device 108 includes a monitoring system which processes sensor data transmitted or read from sensor platform 702. In another embodiment, sensor module 706 includes a monitoring unit and one or more sensors. In one such embodiment, the monitoring unit of sensor module 706 processes the data from the sensors in order to detect particular physiological conditions and communicates data corresponding to the detected physiological conditions to external device 108 for display.

In the example embodiment shown in FIG. 13, sensor platform 702 is triangular in shape. Such a shape can be advantageous for a sensor platform that is to be placed on or around the Xyphoid Process because it conforms better to that portion of the anatomy. The geometry of sensor platform 702 can, however, be selected to meet measurement requirements. For instance, circular shapes or other shapes could be used as dictated by the anatomy, by the types of measurements to be performed, or by manufacturing requirements.

Figure 14A:
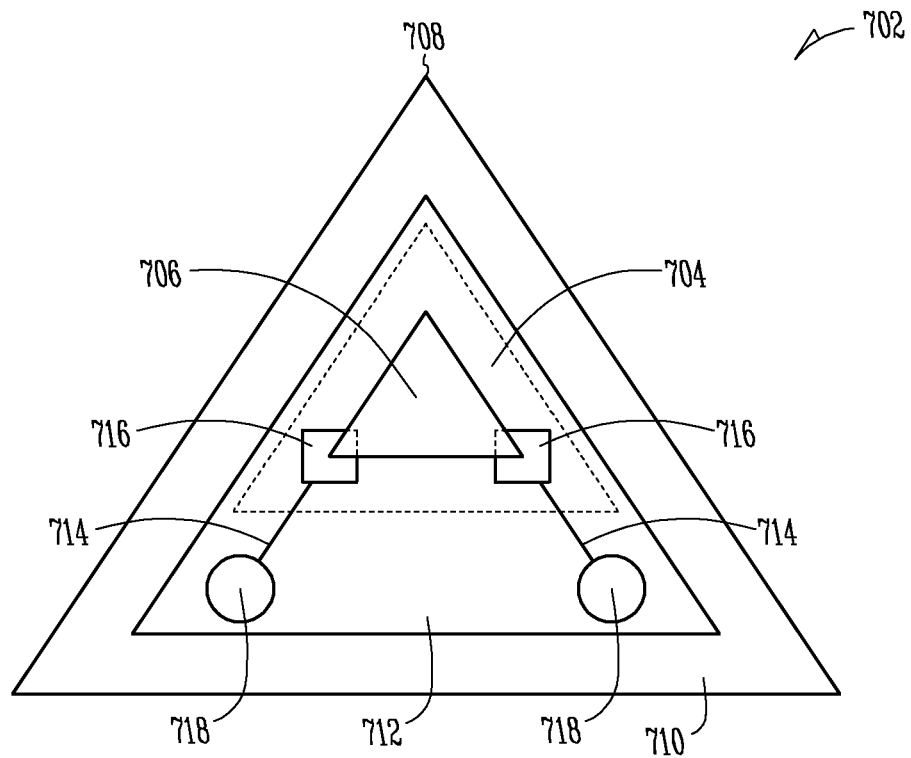
FIG. 14a illustrates a bottom view of another sensor platform that can be used in the system of FIG. 1.
Figure 14B:
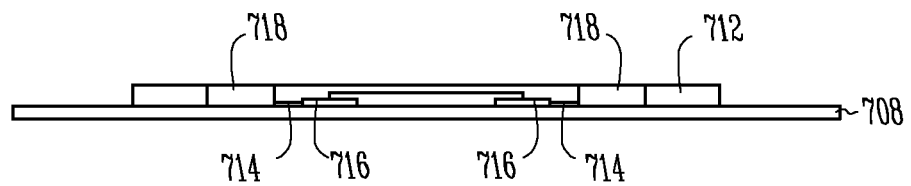

FIG. 14A illustrates a skin-side view of a sensor platform 702 that can be used in the system of FIG. 13. In the example shown in FIG. 14A, sensor platform 702 includes a patch 708 and a sensor pocket 704. Patch 708 includes an adhesive strip 710 used to secure the platform to the body of the subject. The adhesive could be hydrogel, hydrocolloid or other adhesive material, In the example embodiment shown in FIG. 14A, a section of material 712 is positioned on patch 708 so as to form pocket 704. One example embodiment of such positioning is shown in FIG. 14B. In some embodiments, a release sheet (not shown) protects adhesive strip 710. The release sheet is removed from patch 708 at the time of use in order to expose the adhesive and permit placement of the sensor platform on the patient. In one example approach, patch 708, section 712, and pocket 704 are constructed such that, when assembled, they protect the sensor module from the external environment while allowing the enclosed sensor module to detect the requisite physiological attributes of the patient. In one embodiment, sensor module 706 could be any of the monitors discussed for sensor module 106 above.

In one example, section 712 includes a surface protected by one or more release sheets. The surface is exposed by removing the release sheets. The surface is then pressed against the adhesive surface of tape strip 710 to seal sensor pocket 704.

In one approach patch 708 includes a backing material made with hydrophobic polyurethane foam. One advantage of polyurethane foam is that it permits water vapor to escape from the surface of the skin, but keeps liquid water from reaching the surface of the skin. Other backing materials, such as fabric, polyethylene or polyvinyl chloride could be used as well.

It can be advantageous to use a material that is flexible in multiple directions but that still keeps sensor module 706 tight against the skin, since bunching of the backing material and movement of module 706 relative to the skin adds to the signal noise/artifact. One such material is used in the Band-Aid® Activ-Flex™ bandage.

In some embodiments, it can be advantageous to spread out electrodes of sensor module 706 such that there is more separation between the electrodes of sensor module 706. In some such embodiments, as is shown in FIGS. 14A and 14B, one or more electrical conductors 714 are placed between patch 708 and section 712. Each conductor 714 is connected between a pad 716 and a pad 718 such that conductor 714 provides a low resistance path between pads 716 and 718. In some such embodiments, pads 716 are designed to contact the skin of the patient while section 712 insulates conductors 714 and pads 716 from contact with the skin of the patient. In one such embodiment, section 712 includes voids through which pads extend to contact the skin of the patient. In one embodiment, sensor module 706 is designed so that conductors of sensor module 706 contact pads 716 when sensor module 706 is placed in pocket 704. In another embodiment, sensor module 706 is a carrier adapted to receive a sensor device and to connect the device to pads 718. On such carrier is shown in FIG. 17B and described below.

In one embodiment, the conductors and pads for extending the separation between electrodes are formed on the side of patch 708 opposite the skin-facing side. In one such embodiment, pocket 704 is designed to open and close easily in order to facilitate quick change out of sensor modules 706.

Figure 15A:
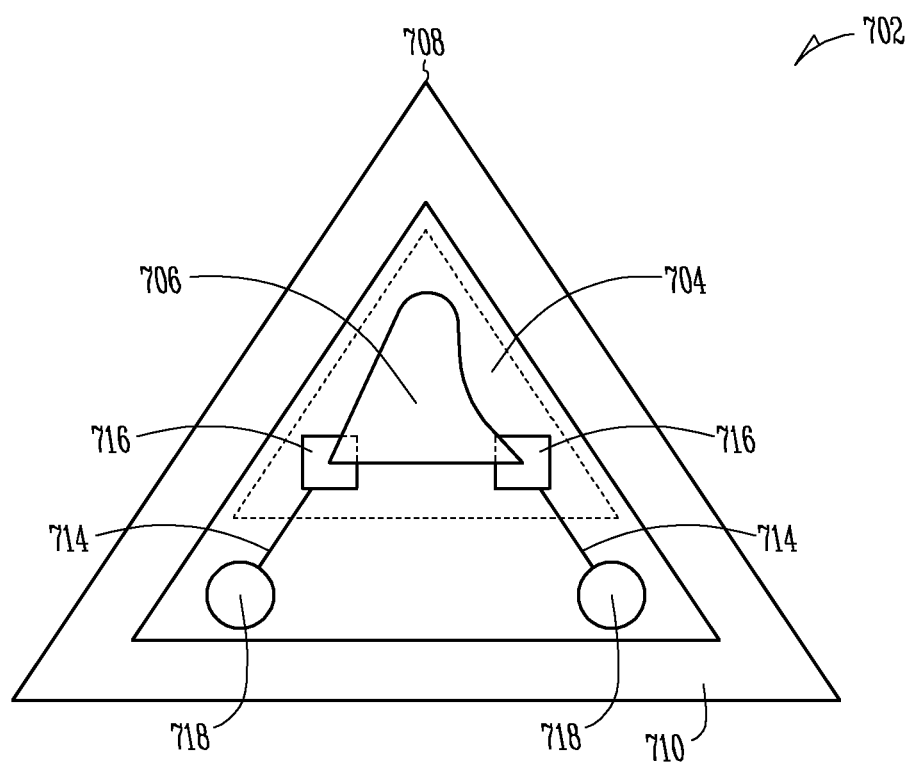
FIG. 15A illustrates a bottom view of another sensor platform that can be used in the system of FIG. 1.

In one embodiment, as is shown in FIGS. 15A-C, pocket 704 and sensor module 706 are designed such that the shape of sensor module 706 conforms to a section of pocket 704 so as to encourage a particular positioning of sensor module 706 within pocket 704. In one embodiment, section 712 includes a depression 705 that is shaped to receive sensor module 706 when it is in the correct position within pocket 704. In one embodiment, section 712 includes a depression 705 that is shaped to receive sensor module 706 when it is in the correct orientation within pocket 704.

In the embodiments shown in FIGS. 15B and 15C, a section of material 712 is positioned on patch 708 so as to form pocket 704. In some embodiments, a release sheet (not shown) protects adhesive strip 710. The release sheet is removed from patch 708 at the time of use in order to expose the adhesive and permit placement of the sensor platform on the patient. In one embodiment, patch 708 includes a backing material made with hydrophobic polyurethane foam. One advantage of polyurethane foam is that it permits water vapor to escape from the surface of the skin, but keeps liquid water from reaching the surface of the skin. Other backing materials, such as fabric, polyethylene or polyvinyl chloride could be used as well.

In one example, section 712 includes a surface protected by one or more release sheets. The surface is exposed by removing the release sheets. The surface is then pressed against the adhesive surface of tape strip 710 to seal sensor pocket 704.

In another embodiment, pocket 704 is not sealed. Instead, either material 712, patch 708 or both have enough elasticity to receive a sensor module 706 and keep it secure and in place in pocket 704. A friction fit could be used as well.

In one embodiment, sensor module 706 is conductively coupled through conductors 714 to pads 718 simply through contact. Other approaches, such as those discussed above, can be used as well.

In the embodiment shown in FIG. 15B, sensor platform 702 includes three electrodes 718. Sensor module 706 measures a parameter such as ECG as a signal measured between two of the electrodes 718. In one such embodiment, sensor module 706 selects the two electrodes 718 that provide the best measurement of, for instance, ECG, as part of a setup process, or as part of calibration, since the best pair of electrodes may change over time or based on each individual's anatomy.

Figure 16A:
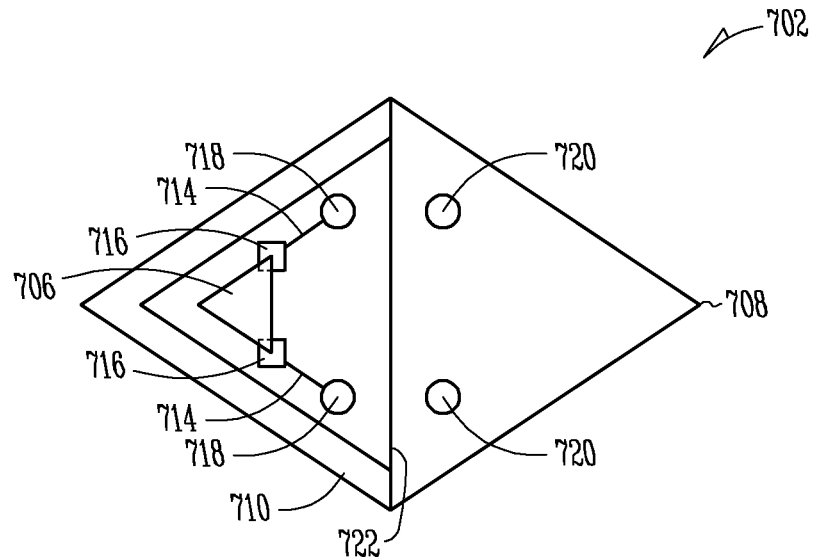
FIGS. 16A-16C illustrate sensor platforms that can be used in the systems of FIGS. 1 and 13.

Alternate embodiments of sensor platform 702 are shown in FIGS. 16A-E. In the embodiment shown in FIG. 16A, sensor platform 702 includes a patch 708 adapted to receive sensor module 706. In some such embodiments, as is shown in FIG. 16A, one or more electrical conductors 714 positioned on patch 708. Each conductor 714 is connected between a pad 716 and a pad 718 such that conductor 714 provides a low resistance path between pads 716 and 718. Sensor module 706 is placed in contact with pads 716. Patch 708 is then folded at axis 722 to form a triangular sensor platform. Adhesive strip 710 helps to keep the two halves of patch 708 together. In one embodiment, sensor module 706 is a carrier adapted to receive a sensor device and to connect the device to pads 718.

In some embodiments, pads 716 are designed to contact the skin of the patient while patch 708 insulates conductors 714 and pads 716 from contact with the skin of the patient. In the embodiment shown in FIG. 16A, voids 720 are provided in patch 708 and are adapted to receive pads 718 such that pads 718 can contact the patient's skin through voids 720. In one such embodiment, a release sheet protects adhesive strip 710 prior to inserting sensor module 706 and a release sheet protects the skin-facing surface of that portion of patch 708 to the right of axis 722 prior to affixing sensor platform 702 to the patient.

Figure 16B:
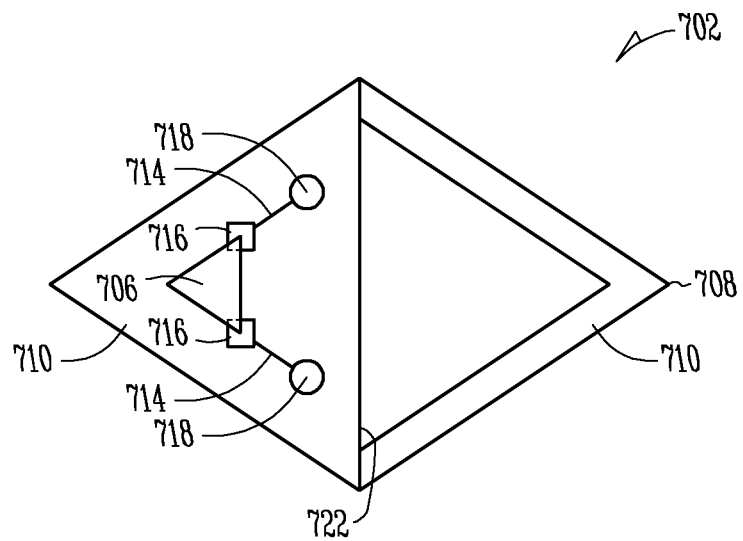

An alternate embodiment of the sensor platform of FIG. 16A is shown in FIG. 16B. In the example embodiment of FIG. 16B, adhesive strip 710 is shown on that portion of patch 708 to the right of axis 722 and voids 720 are on tape strip 708 below pads 718.

Figure 16C:
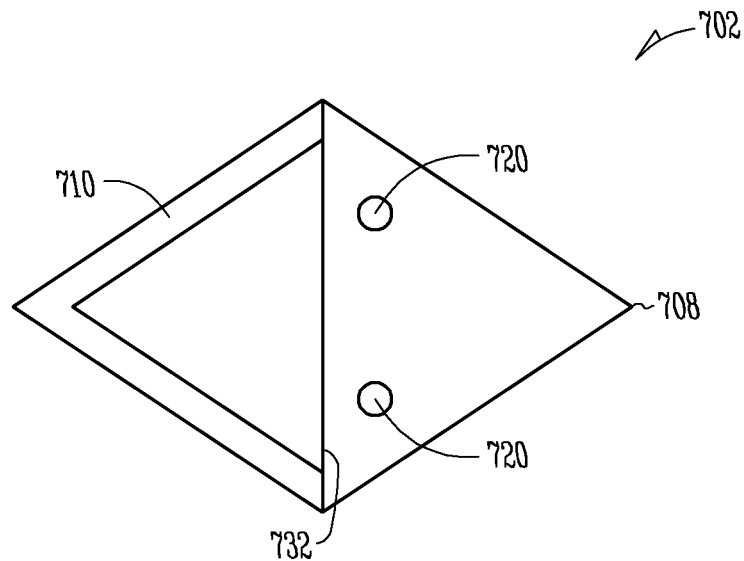
Figure 16D:
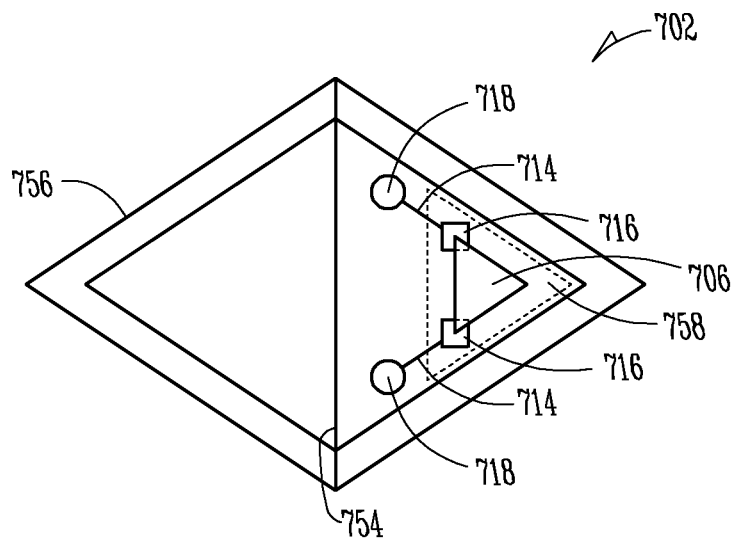
FIGS. 16D-16G illustrate a sensor carrier that can be used in the sensor platform of FIG. 16C.

Yet another alternate embodiment of a sensor platform 702 is shown in FIGS. 16C and 16D. In the embodiment shown in FIGS. 16C and 16D, patch 708 includes an adhesive strip 710 used to seal the two sides of patch 708 when patch 708 is folded in half around axis 732. In one such example embodiment, patch 708 includes voids 720 which accommodate a pad such as pads 718. In one such embodiment, a release sheet protects adhesive strip 710 prior to assembling sensor platform 702 and a release sheet protects the skin-facing surface of that portion of patch 708 to the right of axis 732 prior to affixing sensor platform 702 to the patient. In one embodiment, patch 708 is designed to accommodate a sensor module 756 such as shown in FIG. 16D.

In the example embodiment shown in FIG. 16D, sensor carrier 756 is designed to be positioned in the sensor platform 702 of FIG. 16C inside adhesive strip 710 and on the left side of axis 732. Sensor carrier 756 provides a uniform interface to patch 708. In the example shown, sensor carrier 756 includes a section 758 designed to accommodate a sensor module 706, one or more conductors 714, and pads 716 and 718. Each conductor 714 is connected between a pad 716 and a pad 718 such that conductor 714 provides a low resistance path between pads 716 and 718. In some such embodiments, pads 716 are designed to contact the skin of the patient while section 712 insulates conductors 714 and pads 716 from contact with the skin of the patient. In one embodiment, sensor module 706 is designed so that conductors of sensor module 706 contact pads 716 when sensor module 706 is placed in section 758. In another embodiment, sensor module 706 is an adapter that receives a sensor device and connects the device to pads 716.

Figure 16E:
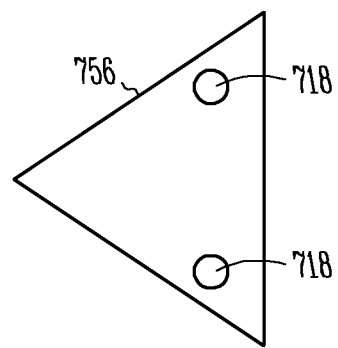

In one embodiment, sensor carrier 756 receives a sensor module 706 having connectors that make contact with pads 716. In one such embodiment, sensor carrier 756 is folded along axis 754 and latches shut mechanically to secure sensor module 706 in contact with pads 716. FIG. 16E illustrates sensor carrier 756 when folded. As can be seen, in the embodiment shown in FIG. 16E, pads 718 extend through the back of sensor carrier 756 such that, when inserted in patch 708, pads 718 extend through voids 720.

In one embodiment, carrier 756 is designed to be reuseable. When the sensor platform 702 is removed from the patient, carrier 756 is disassembled and sensor module 706 is recovered. Such an approach facilitates easy replacement of sensor modules 706 as needed.

Figure 16F:
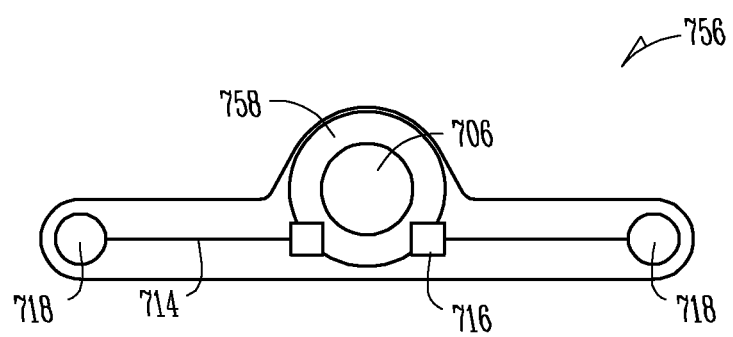

Another example embodiment of carrier 756 is shown in FIG. 16F. Sensor carrier 756 provides a uniform interface to a sensor platform. In the example shown, sensor carrier 756 includes a section 758 designed to accommodate a sensor module 706, one or more conductors 714, and pads 716 and 718. Each conductor 714 is connected between a pad 716 and a pad 718 such that conductor 714 provides a low resistance path between pads 716 and 718. In some such embodiments, pads 716 are designed to contact the skin of the patient while section 712 insulates conductors 714 and pads 716 from contact with the skin of the patient. In one embodiment, sensor module 706 is designed so that conductors of sensor module 706 make an electrical connection with pads 716 when sensor module 706 is placed in section 758. In one such embodiment, sensor module 706 is an adapter that receives a sensor device and connects the device to pads 716.

In one embodiment, sensor carrier 756 receives a battery used to power sensor module 706. In one such embodiment, sensor carrier 756 is adapted to hold the battery in electrical contact with sensor module 706.

In one embodiment, carrier 756 is designed to be reuseable. When the sensor platform 702 is removed from the patient, carrier 756 is disassembled and sensor module 706 is recovered. Such an approach facilitates easy replacement of sensor modules 706 as needed.

Figure 16G:
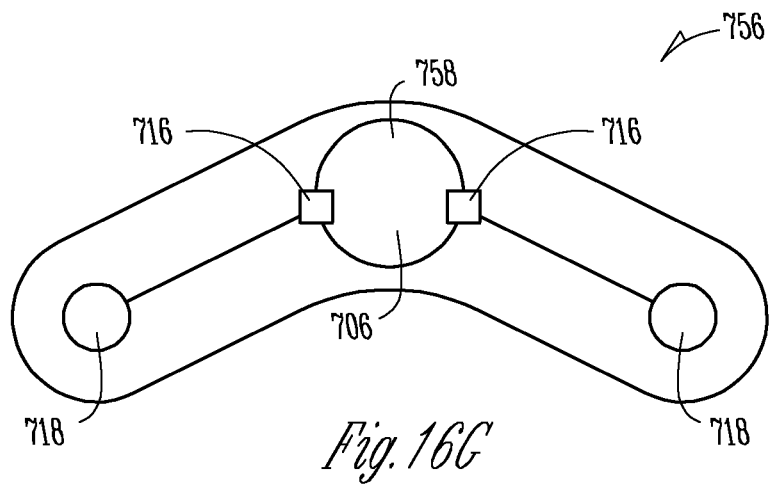

Yet another example embodiment of carrier 756 is shown in FIG. 16G. Once again, sensor carrier 756 provides a uniform interface to a sensor platform, but in a different form factor. In the example shown, sensor carrier 756 includes a section 758 designed to accommodate a sensor module 706, one or more conductors 714, and pads 716 and 718. Each conductor 714 is connected between a pad 716 and a pad 718 such that conductor 714 provides a low resistance path between pads 716 and 718. In some such embodiments, pads 716 are designed to contact the skin of the patient while section 712 insulates conductors 714 and pads 716 from contact with the skin of the patient. In one embodiment, sensor module 706 is designed so that conductors of sensor module 706 make an electrical connection with pads 716 when sensor module 706 is placed in section 758. In one such embodiment, sensor module 706 is an adapter that receives a sensor device and connects the device to pads 716.

In one embodiment, sensor carrier 756 receives a battery used to power sensor module 706. In one such embodiment, sensor carrier 756 is adapted to hold the battery in electrical contact with sensor module 706.

In one embodiment, carrier 756 is designed to be reuseable. When the sensor platform 702 is removed from the patient, carrier 756 is disassembled and sensor module 706 is recovered. Such an approach facilitates easy replacement of sensor modules 706 as needed.

Figure 16H:
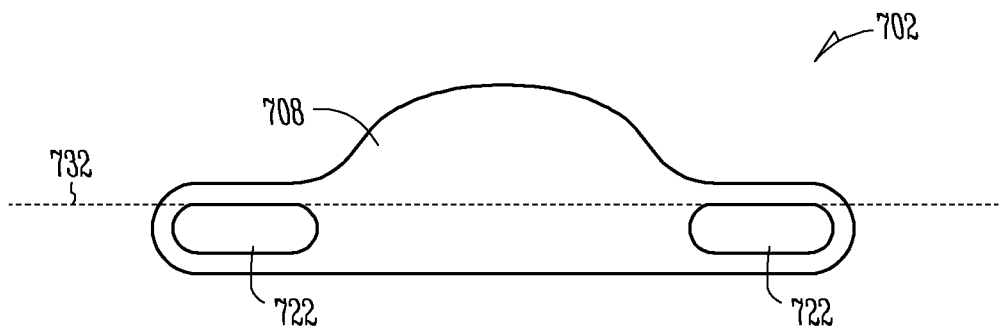
FIGS. 16H-16I illustrate sensor platforms that can be used in the systems of FIGS. 1 and 13.

An example embodiment of a sensor platform 702 capable of receiving sensor carrier 756 of FIG. 16F is shown in FIG. 16H. In the example embodiment shown in FIG. 16H, sensor carrier 756 is designed to be positioned between contact windows 722. Sensor platform 702 is formed, in one embodiment, from a non-conductive adhesive material 708. In one embodiment, material 708 is formed from a material suitable for enhanced skin care (e.g., hydrocolloid-aloe vera). In one embodiment, windows 722 include a material such as a hydrocolloid enhanced for electrical conductivity. In the embodiment shown in FIG. 16H, material 708 folds on axis 732 to secure sensor carrier 756 within a pocket 704.

The example sensor platform 702 of FIG. 16H can also receive a sensor module 706 with external electrodes.

Figure 16I:
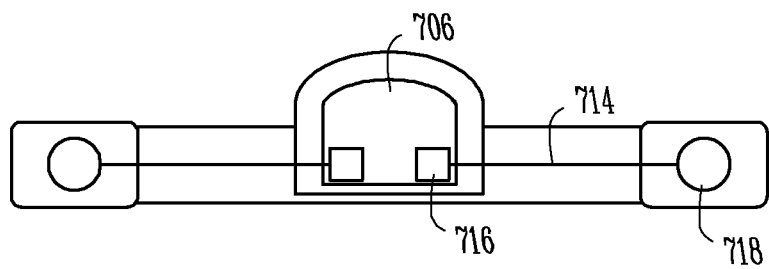

Another embodiment of sensor platform 702 is shown in FIG. 16I. In the example embodiment of FIG. 16I, sensor platform 702 includes integrated contacts 718 connected through conductors 714 and contacts 716 to a sensor module 706 or to a sensor carrier 756. In the example given in FIG. 16I, contacts 718 are placed in contact windows 722 and, in one embodiment, extend through windows 722 to make contact with the skin. In another embodiment, windows 722 include an electrically conductive hydrocolloid pad interposed between contact 718 and the skin to enhance electrical conductivity.

Figure 17A:
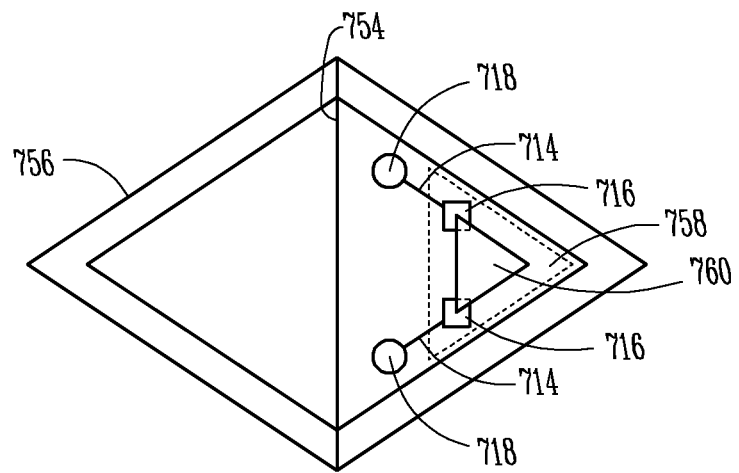
FIG. 17A illustrates another sensor carrier that can be used in the sensor platform of FIG. 16C.
Figure 17B:
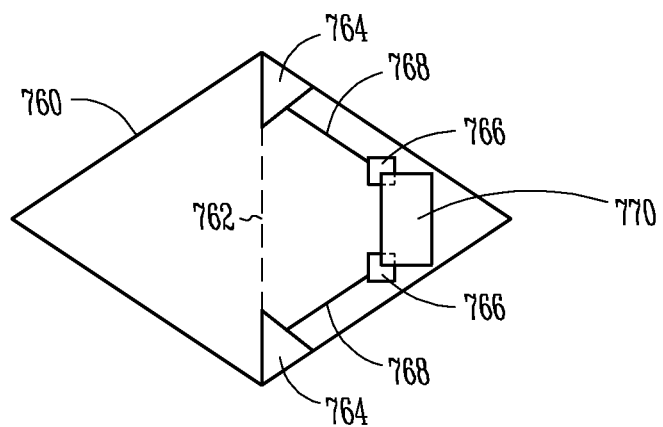
FIG. 17B illustrates a sensor device adapter that can be used in the sensor carrier shown in FIG. 17A.

Another embodiment of sensor carrier 756 is shown in FIG. 17A. In the example embodiment of sensor carrier 756, section 758 receives a sensor device adapter 760 used to adapt sensor devices to sensor carrier 756. One example of sensor device adapter 760 is shown in FIG. 17B. The sensor device adapter of FIG. 17B includes two halves that fold around axis 762. A sensor device 770 is placed within sensor adapter 760 and adapter 760 folds along axis 762 to enclose sensor device 770 and keep sensor device 770 in contact with pads 766. Pads 766 connect via conductor 768 with pads 764, and, when assembled as shown in FIG. 17A, through pads 764 to pads 716. Such an approach provides a standard interface for adapting a variety of sensor devices to sensor platforms 702. In one such approach, manufacturers of such devices can use sensor device adapters such as described above to configure their devices to work with sensor carriers 756.

Other approaches for enclosing sensor device 770 within sensor adapter 760 are contemplated as well. For instance, sensor device 770 can be enclosed by mating two separate sides of adaptor 760.

Figure 18A:
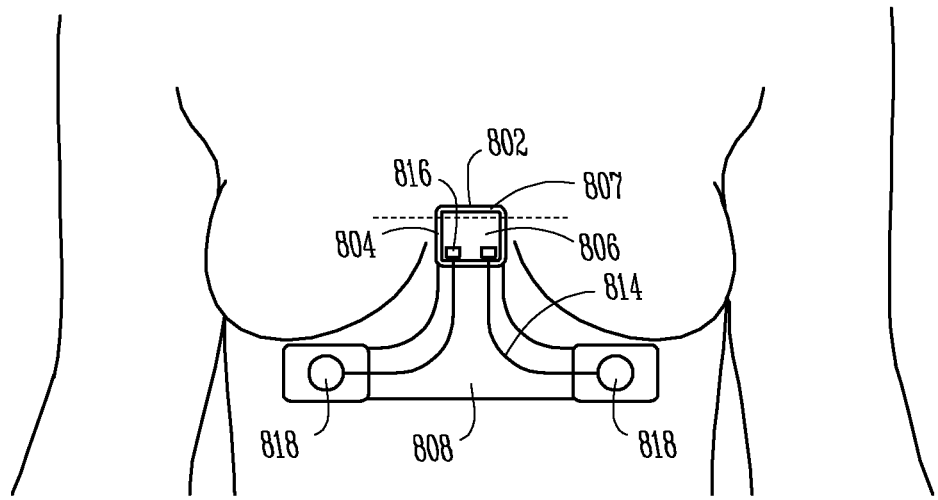
FIGS. 18A-18C illustrate sensor platforms that can be used in the systems of FIGS. 1 and 13.

Sensor packages can be adapted to gender. An embodiment adapted for the female anatomy is shown in FIG. 18A. In the sensor platform 802 of FIG. 18A, adhesive platform 808 includes electrodes 818, and an envelope-like pocket 804 that receives a sensor module 806. Contacts in sensor module 806 are electrically coupled through contacts 816 and conductors 814 to electrodes 818. In one embodiment, sensor module 806 senses an ECG via two or more of the electrodes 818. Other sensors can be included, such as accelerometers or GPS systems, depending on the application.

In one embodiment, a sealable flap 807 is included. It can be used to seal envelope 804 to contain and protect sensor module 806 after it is inserted.

In the embodiment shown in FIG. 18A, adhesive platform 808 is shaped to place contacts 818 far apart on the chest. Wider electrical spacing creates a better ECG vector and, in some cases, can be used to measure respiration and transthoracic impedance (to measure, for instance, pulmonary edema). In one embodiment, pocket 804 includes a third contact 818 (not shown) and sensor module 806, or other configuration apparatus, chooses the best two out of the three contacts 818 to measure ECG.

In one embodiment, contacts 818 extend through platform 808 to touch the skin. In another embodiment, contacts 818 are conductively couple to the skin through electrically conductive pads or gels formed within platform 808.

Figure 18B:
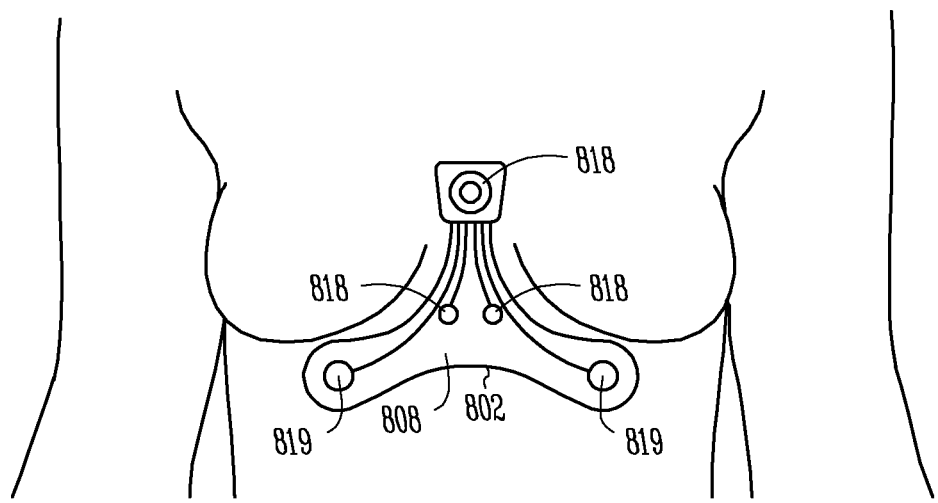

Another embodiment adapted for the female anatomy is shown in FIG. 18B. In the sensor platform 802 of FIG. 18B, adhesive platform 808 includes electrodes 818 and 819, and a pocket that receives a sensor module 806. Contacts in sensor module 806 are electrically coupled to electrodes 818 and 819. In one embodiment, sensor module 806 senses an ECG via two or more of the electrodes 818. In one embodiment, sensor module 806 senses respiration via electrodes 819. In one such embodiment, heart failure can be detected via changes in transthoracic impedance. In another embodiment, a strain gauge measures thoracic or diaphragmatic changes. Other sensors can be included, such as accelerometers or GPS systems, depending on the application.

Figure 18C:
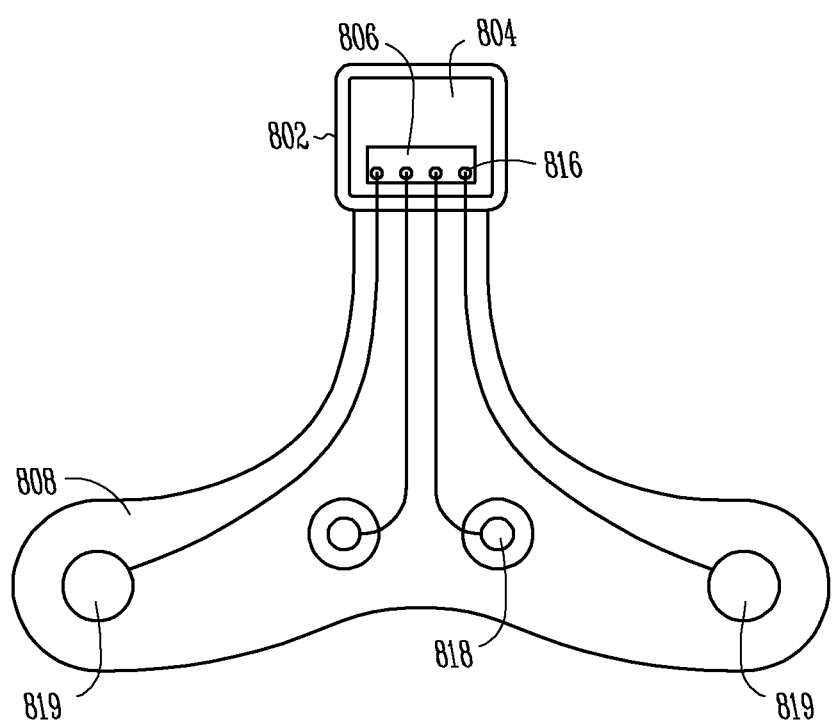

An alternate embodiment of sensor platform 802 is shown in FIG. 18C. In that embodiment, platform 802 includes a pocket 804 for receiving a sensor module 806. Sensor module 806 is electrically connected to electrodes 818 and 819 through contacts in pocket 804. Once again, in one embodiment, sensor module 806 senses an ECG via two or more of the electrodes 818. In one embodiment, sensor module 806 senses respiration via electrodes 819. In one such embodiment, respiration is measured via skin impedance. In another embodiment, a strain gauge measures thoracic or diaphragmatic changes.

In one embodiment, ECG sensors 818 couple to the skin of the female subject via electrically conductive adhesive pads or windows.

The advantage of the embodiments shown in FIGS. 18A-C, are that the designs configure more closely to the female anatomy. For instance, as can be seen in FIGS. 18A-C, one end of platform 802 can be placed higher on the chest. This can be advantageous since it places the sensor pocket 804 between the breasts and above the bra line.

Platform 802 can be adapted to detect heart failure by measuring impedance via an impedance sensor, or to measure respiration via measurements of thoracic or diaphragmatic changes.

In one embodiment, contacts in sensor module 806 are electrically coupled through electrodes 816 to electrodes 818. In one such embodiment, the contacts are electrically coupled through contact between sensor module 806 and electrodes 816. In another embodiment, the contacts are electrically connected through snap connectors built in to platform 802.

Integrative Lifestyle Monitor

System 100 can be used as an integrative lifestyle monitor. The lifestyle monitor could be used in humans to identify what the individual is doing and their physiological state and to recommend optimization strategies based on the individual's goals and physiological state.

In animals, the lifestyle monitor could be used to track the animal's physiological parameters and training and suggest changes in their training regime. For example, the lifestyle monitor could be used to track a racehorse's physiological parameters and training routine and to suggest changes in their training routine.

A human-based example is discussed next.

With the rising incidence of chronic disease and the escalating cost of healthcare there has been increasing focus on wellness, prevention and lifestyle modification. Much of the focus has been on getting enough exercise, proper nutrition, maintaining a healthy weight, smoking cessation, medication compliance and managing stress. Non-medical consumer healthcare tools and technology have emerged to assist individuals in tracking and measuring their progress toward changing their behaviors and achieving these goals. Examples include physiological monitoring technology such as a heart rate monitor that can be worn on a chest strap tracking an individual's heart rate, heart rate variability, calories burned; target heart rates, distances traveled etc to monitor exercise performance. Another example of a lifestyle modification monitor is a caloric expenditure and activity tracker affixed with a strap, clip, or other similar means to an individual's arm, belt, clothing, jewelry or wrist. These devices alone or in combination with user input such as food consumption can assist individuals with monitoring progress in achieving their goals related to weight loss by measuring calories consumed vs. calories expended. While these devices are helpful, they are still relatively cumbersome to wear and cosmetically conspicuous for 24/7 use. For example the sensor housing for the Polar Model T31 heart rate monitor's chest strap is 12×1 inches and the dimensions for the sensor housing of the commercially available caloric expenditure device, BodyBugg® is 2×2 inches. This makes 24 hour continuous monitoring inconvenient especially when daily activities such as bathing or sleeping are factored in since these devices are typically not waterproof. Concerns with size, comfort, and cosmetics are especially applicable when applied to a growing market, prevention of childhood obesity.

Besides the concerns of size, comfort, appearance and interference with activities of daily living, another drawback to the current use of these monitoring technologies is that their intended use is for tracking and monitoring physiology while an individual is actively engaged in changing their behavior. While this is certainly a good thing, it is well known that many people successfully achieve fitness, diet or weight loss goals in the short term while they are actively and consciously focused on these goals but gradually turn their attention back to the demands of daily living and often fall back into preexisting unhealthy habits and behaviors.

More and more research shows helping people transform unhealthy habits and behavior involves addressing the systems surrounding the individual's lifestyle. These systems represent both an internal and external perspective of the individual. Many public and community health programs have focused on ensuring the individual's external environment is supportive of healthy choices (by providing access, for example, to recreation opportunities, community gardens, health screenings, healthy workplaces, and health promotion education). Equally important if not fundamentally more important is a systematic approach to supporting individuals in understanding the internal system surrounding their lifestyle choices. This includes understanding the conscious and unconscious patterns of thoughts, emotions, beliefs and behaviors and their resultant effects on physiology. In other words, understanding how the individual responds or adapts to the various mental, emotional, physical or environmental stressors they encounter throughout their day and the cumulative effect of this response on many biological processes. Research continues to demonstrate a strong correlation between the deleterious cascading electrical and chemical physiological effects of negative thoughts and emotions and the development and progression of medical conditions and chronic diseases such as heart disease, hypertension, stroke, high cholesterol, obesity, metabolic disorders, diabetes, insulin resistance, pain, anxiety, mood disorders, and depression. However, it is not the mere experience of these stressors but rather the nature of the activation and recovery patterns including intensity, duration, oscillation, resiliency and speed of recovery from these stressors that has the greatest impact on health, performance, mood, behavior and overall well-being. Through the corresponding release of various hormones, neurotransmitters, cytokines and catecholamines associated with activation patterns of the sympathetic nervous system various physiological processes can become imbalanced and directly affect health, performance, habits, behaviors, choices, mood and vitality.

There are many challenges however in supporting individuals in understanding the states of their own internal system. One of the obvious challenges is the ability to be consciously aware and accurately perceive our unconscious and automated response happening within the body. Nearly all stimuli is immediately assessed by the brain for emotional content and if initially perceived as a threat, loss, or fear from either a mental, emotional or physical perspective our body has a built in physiological response mechanism to protect and prepare us for the challenge at hand. Through the HPA axis (hypothalamus, pituitary, adrenal axis) chemical and electrical commands are instantaneously initiated throughout the body. This response has often happened faster than the conscious registration of the stimuli by the cognitive centers within the brain. However the stimuli is simultaneously sent down a pathway for further analysis where logic/reasoning, memory, and behavioral response are contextually applied to the event and a conscious response to the stimuli is now likewise although more slowly communicated electrically and chemically throughout the body. While there is not as much that we can do to control the nearly instantaneous and automated response of our body to protect and prepare us for a potential threat, we do have a greater ability to control the secondary conscious processing and as a result can influence our mental, emotional, behavioral and physiological responses and overall well-being.

Capturing Life on Auto Pilot: What is needed therefore is the ability to monitor on a continuous and periodic basis an individual's physiological responses to the mental, emotional, physical or environmental stressors as they are encountered throughout the day in order to: characterize their overall level of variability between the sympathetic and parasympathetic branches both at rest and during activity, identify what stimuli triggers the autonomic response of "fight or flight", if and when that response is mitigated or balanced by the conscious processing pathway, if and when the stress response is sustained or actually initiated through the conscious processing of thoughts, emotions and behavioral planning; and to quantify and characterize the intensity, duration, oscillation, resiliency and recovery of mental, emotional, physical or environmental stress as experienced on a daily basis and to correlate this effect to the associated biological pathways.

System 100 can be used to monitor a number of daily activities. In one example approach, diet, nutrition and the biological composition of caloric intake are monitored and can be used to correlate the cause and effect nature nutrition has on physical, mental and emotional states. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. via nutritional intake. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns. In another example approach, physical activity is monitored and its effect on emotional and mental state is measured. In one such approach, exercise or physical activity is monitored in relation to mood and behavior influencing biochemicals, e.g., endorphins, epinephrine, norepinephrine, cortisol, and dopamine. Physical activity may also be monitored for its influence on autonomic activity in particular parasympathetic gain or control after exercise recovery. Parasympathetic gain or control post exercise may then be correlated to physical, mental or emotional experiences by the subject and may be identified as an effective strategy for recovery from particular mental or emotional patterns or states. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. via physical activities for example cardiovascular activities or mind/body balancing activities such as yoga. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

In another example approach, a subject's sleep or periods of rest is monitored and its effect on physical, emotional and mental state is measured. Cause and effect correlation can then guide an individual in implementing personalized strategies via sleep/rest patterns that optimize mood, performance, vitality, health etc. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. via sleep/rest patterns. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

In another example approach, the efficacy of stress management or resiliency techniques is assessed. In one such approach, the effects on the autonomic nervous system, such as gain and control in the parasympathetic branch could be monitored as well as overall changes in the coherence or entrainment between the parasympathetic and sympathetic branches. In one embodiment, these physiological changes are correlated to the subject's physical, mental and emotional experience as an effective tool for changing behavior, underlying beliefs, and neuropathways. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. via stress management, relaxation or resiliency techniques. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

One method for monitoring the parasympathetic branch of the nervous system of an individual involves capturing, via a cardiac sensor, data representing heart rate activity, capturing movement data via an accelerometer, processing the data from the cardiac sensor and the movement data from the accelerometer to look for patterns of heart rate recovery and patterns of increasing heart rate variability and displaying changes in the patterns of heart rate recovery and patterns of heart rate variability over time. In one embodiment, the accelerometer is used to help the processor distinguish between sources of changes in heart rate activity.

Another method for monitoring the parasympathetic branch of the nervous system of an individual involves capturing, via a respiration sensor, data representing breathing patterns, capturing movement data via an accelerometer, processing the data from the respiration sensor and the movement data from the accelerometer to look for patterns of heart rate recovery and patterns of increasing heart rate variability and displaying changes in the patterns of heart rate recovery and patterns of heart rate variability over time. In one embodiment, the accelerometer is used to help the processor distinguish between sources of changes in breathing patterns.

A method for monitoring performance of the branches of the autonomic nervous system of an individual will be described next. In one example embodiment, the method includes capturing, via a cardiac sensor, data representing heart rate activity, capturing movement data via an accelerometer, processing the data from the cardiac sensor and the accelerometer to capture activation and recovery patterns of the nervous system as a function of the cardiac sensor data and the movement data and displaying the activation and recovery patterns. In one embodiment, the accelerometer is used to help the processor distinguish between sources of changes in heart rate activity.

Another method for monitoring performance of the branches of the autonomic nervous system of an individual includes capturing, via a respiration sensor, data representing breathing patterns, capturing movement data via an accelerometer, processing the data from the respiration sensor and the accelerometer to capture activation and recovery patterns of the nervous system as a function of the respiration sensor data and the movement data and displaying the activation and recovery patterns. In one embodiment, the accelerometer is used to help the processor distinguish between sources of changes in breathing patterns.

In one such embodiment, processing includes contextualizing the captured activation and recovery patterns to activities by the individual. These activities may include physical activities, nutritional intake, emotional or mental processing, physiological aspects of the individual (e.g., underlying medical conditions), time of day, location of the individual, the environment, etc.

As noted above, long term monitoring of physiological activity can be used to train an individual. One method for enhancing tone and control of the branches of the autonomic nervous system of an individual will be described next. In one example embodiment, the method includes capturing, via a cardiac sensor, data representing heart rate activity, capturing movement data via an accelerometer, processing the data from the cardiac sensor and the accelerometer to capture activation and recovery patterns of the nervous system as a function of the cardiac sensor data and the movement data, contextualizing the captured activation and recovery patterns to aspects of the individual and conveying recommendations to the individual.

One aspect of the individual used to contextualize the captured activation and recovery patterns is the individual's behavior (such as nutrition, physical activities, sleep/rest patterns, relaxation activities, stress management techniques, etc.). Another aspect of the individual used to contextualize the captured activation and recovery patterns is the individual's patterns of daily living. Another aspect of the individual used to contextualize the captured activation and recovery patterns is the individual's processing of mental and emotional stimulus. Another aspect of the individual used to contextualize the captured activation and recovery patterns is the individual's underlying medical condition or their genetic predisposition. The captured activation and recovery patterns can be further contextualized to take into account movement by the individual as tracked by the accelerometer, or as tracked by a GPS device.

In another example approach, weight control activity is monitored and its correlation to patterns of physiological stress is monitored. This approach has the advantage of identifying triggers of emotional eating or particular behavior patterns as well as the relation of these patterns to underlying patterns of physiological stress. This approach can also identify where physiological pathways controlling digestion, metabolism, and energy consumption may be less effective or resilient due to the deleterious chemical effects of chronic stress. For instance, estimated calories consumed vs. calories expended is the foundational formula for estimating weight gain or weight loss. For some individuals, this formula may not actually be corresponding to actual weight management results. In this case, identifying the patterns of physiological stress may be beneficial in identifying a potentially negative effect of chronic elevated cortisol levels associated with prolonged physiological stress and its know effect to disrupt healthy metabolic processes including its affect on fat storage especially within adipose tissue. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. via nutritional intake, physical activity and stress management techniques. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

In another example approach, physical activity is monitored and its effect on emotional and mental state is measured. In another example approach, the effects of substances such as stimulants or suppressants, caffeine, alcohol, nicotine and sugar are studied and their effect on physical, emotional and mental state, and underlying physiology, is measured.

In another example approach, hypertension is measured and its correlation to patterns of physiological stress is monitored. This approach has the benefit of giving individuals feedback on cause and effect patterns of their physical, mental and emotional states on blood pressure measurements. This approach also affords the opportunity to monitor the intensity and duration of sympathetic dominance and provide feedback or alerts to the individual to intentionally build parasympathetic tone, control and resiliency at a certain time or for a specific duration. This can ultimately assist the individual in controlling hypertension without the need for medication. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

In another example approach, high cholesterol is measured and its correlation to patterns of physiological stress is monitored. This approach has the benefit of giving individuals personalized feedback on cause and effect patterns of nutritional intake, exercise, medication, and/or stress management on hyperlipidemia.

In another example approach, glucose levels are measured and correlated to corresponding patterns of physiological stress. This has the benefit of quantifying the effect of physical, mental and emotional stress on glucose or insulin levels independent of dietary intake. This allows patients to have personalized objective data quantifying the benefits of stress management and resiliency techniques in managing metabolic disorders such as diabetes or pre-diabetes. Patterns of physiological stress can also be monitored and the corresponding effect on physiological imbalances throughout the body can be inferred, predicted, or correlated to the individual's actual experience. Strategies can then be recommended to balance the internal physiological environment and optimize mood, cognitive performance, vitality etc. Patterns of physiological stress may be derived from cardiac sensor data or respiratory sensor data or a combination thereof and contextualized using concurrent accelerometer data alone or in combination with GPS data to detect movement and therefore deduce the nature of physical activity in relation to autonomic nervous system patterns.

Physiological data can be used to characterize, predict and modify emotional and mental state. Feedback can be a critical tool in a feedback system used to modify a person's behavior. In one embodiment, system 100 presents the feedback via an external device such as a computer system or a smart phone. For example, in a human, one would identify and recommend optimization strategies based on the individual's goals. In a racehorse, one would identify and recommend to the trainer changes in the horse's training routine. In one example, the presentation of that feedback on external device 108 is tuned to the subject's strengths.

Applications of Physiological Monitoring and Analysis with Context

Some examples of methods of using the sensor platforms described above are discussed next. Sensor modules such as sensor module 106, whether implanted or worn in a sensor platform, can be used to monitor, for example, exercise performance, caloric expenditure, an/or cardio training, including ECG derived activity, and for long periods of time due to their unobtrusive nature.

The integration of multiple sensors in the sensor module and in the sensor platform allows integrated performance data such as motion tracking (cadence, speed, alignment) of limbs alone or in combination with heart rate monitoring for activities such as a golf swing, cyclists, runners, swimming, tennis, throwing, boxing. Such devices can be used to increase performance in athletes or can assist individuals in tracking improvements such as range of motion during physical rehabilitation or recovery from injuries.

Wireless and reusable sensor devices with disposable adhesives have the added benefit that they can be used to collect vital signs of patients with minimum patient discomfort. The vital signs include ECG, temperature, respiration, SO2, and fluid status such as pulmonary edema.

Such devices offer promise in a wide variety of settings, e.g., in hospital settings, in Emergency Room triage, for monitoring patients during transportation or transfers, for monitoring patients during MRI or fMRI, in long-term care facilities and nursing homes, and in sleep disorder and sleep studies. In one embodiment, MRI safe implantable technology is used to monitor vital signs during MRI without implant.

These devices also offers benefits over devices such as holter monitors, single use adhesive monitors and larger adhesive devices in arrhythmia monitoring and diagnosis, These devices can be used, for example, to monitor vulnerable periods such as post MI, post Ablation, the introduction of new medications, cardiac rehab, to monitor transient events such as AF, Syncope, Brady cardia, and Tachycardia, and while targeting prescriptions such as antidepressants or anti-anxiety medications based on ANS activity patterns.

In pediatric and neonatal applications these devices can be used to monitor vital signs or to monitor for stress or for Sudden Infant Death Syndrome. These devices can also be used to monitor patients who might be at risk during exercise. For example, they can be used to monitor athletes at risk for Sudden Arrhythmia Death Syndrome, or to monitor progressed chronic disease states.

The devices can be used for therapy delivery or monitoring. For example, the devices can be used to stimulate nerves in, e.g., TENS or spinal cord stimulation, to stimulate muscles in, e.g., relaxation or muscle strengthening, in treating paralysis or in physical rehabilitation, and to control therapy delivery devices such as implantable or external pumps, stimulation devices (e.g., spinal cord stimulation devices), vagal nerve stimulation and gastric stimulation.

The devices can be used to monitor electromagnetic interference or radiation exposure within an individual's work or home environment.

The devices can be used to monitor or measure autonomic nervous system tone and control (i.e., stress and relaxation activity, resting or nighttime HRV, biofeedback or stress management, positive and negative emotional states, and mind/body techniques or treatments. Such measurements can be useful as diagnostic information for immune disorders, inflammatory disorders, cardiovascular or heart disease, diabetes, cancer, weight disorders, hypertension, and high cholesterol, and for mental health diagnosis and treatment of depression, anxiety, PTSD, ADD/ADHD, OCD, Dementia, Alzheimer and addictive disorders. The measurements can also be useful for monitoring and measuring stress levels for individuals in military combat, for pilots, surgeons, and commercial drivers, for athletes, for pregnant women, for personal and professional development programs, for spas, for executive wellness programs, for medication monitoring and drug titration, for integrative medicine or preventative medicine programs, for genomic or proteomic personalized and predictive medicine, for fitness, wellness, and weight loss programs, for monitoring the effect of physical and social environments on physiology, for vulnerable populations such as foster care, physically or mentally handicapped, elderly, violent or abusive homes, and for brain health, neurogenesis, memory, concentration and focus, mood, resiliency training, rewiring neuropathways, and neurotransmitters.

Finally, the devices can be used as wellness monitoring devices used to monitor or measure parameters such as heart rate, activity levels, cardiovascular training, caloric expenditure, caloric intake, HRV training, sleep measurements, nighttime HR, and HRV. Such measurements can be used to correlate physiology to behaviors, thoughts or emotions, to identify patterns of behavior and the influence of health related activities of daily living, to measure performance and track changes, and for monitoring lifestyle and behavior modification training.

Such devices also offer promise as unobtrusive patient tracking devices. They could also be used to track soldiers in combat situations and to monitor their vital signs while doing so. The likewise could be used to track the location of children, the elderly, children on field trips, and athletes or outdoorsmen entering hazardous or remote environments. In addition, personal information such as personal identification or medical records could be stored in the sensor module and accessed in case of emergency.

The sensor platforms described above can be used for research purposes, for health risk assessment and for personal or professional development. They provide the ability to track subjects 24/7, providing continuous data for specific periods of time outside of a clinical monitoring environment and without the need for implantable or bulky sensor acquisition devices. The research could include mind/body research applications for example ECG and EEG sensor correlations during daily activity, monitoring the effect of pharmacological agents on ECG or other parameters and other medical or physiological research applications.

The sensor platforms can be used for health risk assessment. They provide the ability to capture daily patterns of physiology and behavior in order to estimate current and future risk profiles Risk profile of aggregated populations such as employee base for insurance/wellness assessments; military; schools Individual risk profiles for prevention, genomics and lifestyle modification programs Prediction of the progression of chronic diseases in individuals or populations Assessments for early identification, intervention or diagnosis of depression, anxiety, chronic stress, anger etc.

Finally, the sensor platforms can be used for personal and/or professional development. Using physiological data alone or in combination with user input data to identify unconscious patterns of thoughts, emotions, and/or behaviors Correlation of thoughts and emotional states to physiological states in order to create personalized profiles and diagnostic algorithms Correlation of physiology to behaviors in order to better understand cause and effect such as binge eating during states of high emotional stress Using physiology to identify emotional and/or mental triggers Using physiology to identify recovery, resiliency and rest (or lack thereof) from mental and/or emotional states Creating alerts or feedback mechanisms for individuals to bring conscious awareness to the current state Monitoring the effectiveness of interventions such as meditation, biofeedback, breathing, reflective thinking, etc. in altering physiology Identifying patterns of excuses around daily thoughts, emotions and behaviors Correlating personalized physiology and context to customized educational materials for instance through accessing expert data bases. Search engines, or custom applications that identify and connect individuals to relevant scientific or educational content for instance websites, journal articles, clinical studies, books or other media, training programs, community resources, restaurants, music, classes, experts, based on their personalized preferences and monitored data.

The methods, systems and devices described above can be used to deliver a platform for personalized integrative wellness monitoring and training. The platforms provide objective, personalized data for each individual. That data is monitored and measured for wellness factors such as activation and recovery from stress. The systems and platforms described are used to help an individual understand their body by providing contextual correlation for cause and effect responses to external and internal stimuli, and to provide personalized education, training and resources as a function of the monitoring. For example, specific combinations such as ECG and accelerometer monitors provide information that can be adapted to specific purposes, such as to monitor and enhance fitness training, or to detect and monitor activities and their effects over a day, a week or other time period. Systems can be designed that monitor wellness parameters such as nutrition, caloric intake vs. expenditure, sleep, exercise and autonomic nervous system tone, control and resiliency. The physiological data is then integrated with contextual data to show daily living patterns and to derive cause and effect correlations.

In one embodiment, system 100 is a system for monitoring the autonomic nervous system. In one such embodiment, the system includes a cardiac sensor, an accelerometer and a processor. The cardiac sensor monitors heart rate activity. The processor determines from data captured by the accelerometer and data captured by the cardiac sensor whether a physiological stress response is driven by other than physical activity.

In such an embodiment, the cardiac sensor could be, for example, a cardiac monitor, a loop monitor, or an optical or acoustical sensor for measuring pulse rate.

The combination of an accelerometer and a cardiac sensor allows one to determine if the physiological response is driven by other than physical activity. For instance, if the processor detects patterns such as a rise in heart rate, sympathetic dominance of heart rate variability, or low variability over an extended period of time, and the accelerometer data does not indicate movement that would correlate with that type of cardiac response, one can determine that the response is unlikely to be due to meeting physical demands.

In another embodiment, a system for monitoring the autonomic nervous system includes a respiration sensor, an accelerometer and a processor. The respiration sensor monitors breathing patterns. The processor determines from data captured by the accelerometer and data captured by the respiration sensor whether a breathing pattern is driven by other than physical activity.

The combination of an accelerometer and a respiration sensor also allows one to determine if the physiological response is driven by other than physical activity. For instance, if the processor detects changes in respiration such as rapid breathing, shallow breathing, changes in oxygen level in the blood, and the accelerometer data does not indicate movement that would correlate with that type of change, one can determine that the response is unlikely to be due to meeting physical demands.

In one embodiment, the system for monitoring the autonomic nervous system further includes a global positioning satellite (GPS) device. The GPS device can be used in conjunction with the accelerometer to correlate exercise physiology to movement over a particular area. For instance, a runner might monitor performance of his autonomic nervous system over a particular route over a period of time in order to see the effects of training.

The methods, systems and devices described above can also be used to deliver a platform for personalized monitoring of physical, mental and emotional state and to manage medication as a function of that state. They can be used to monitor and diagnose issues related to the heart, the brain or the vagal nerve, or simply for monitoring body functions relevant to vulnerable populations such as infants, the elderly or the mentally handicapped. Finally, they can be used a part of a system for remote disease diagnosis and management.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

Figure 19:
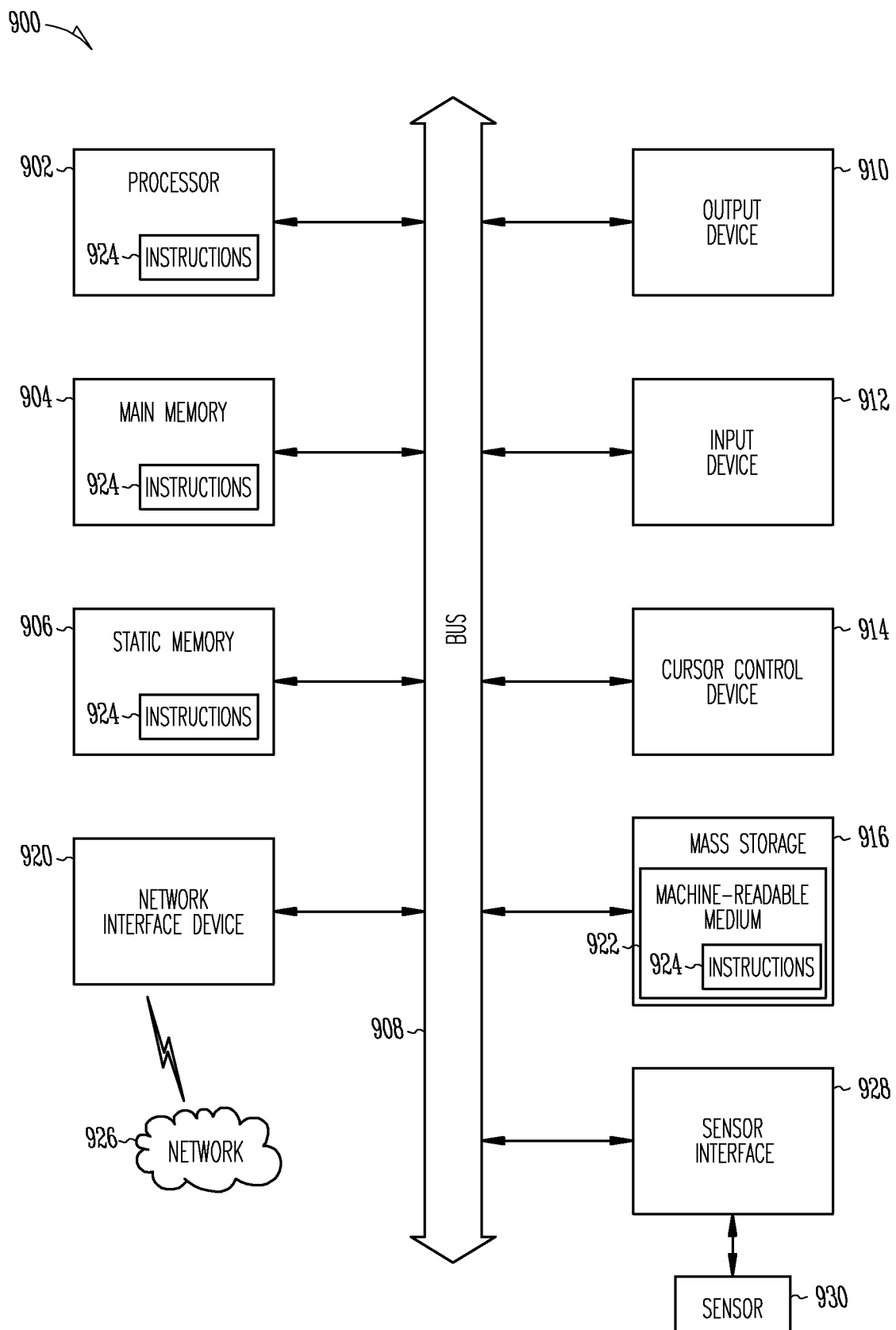
FIG. 19 illustrates a computer-implemented system for physiological monitoring, according to various embodiments of the invention.
Figure 20:
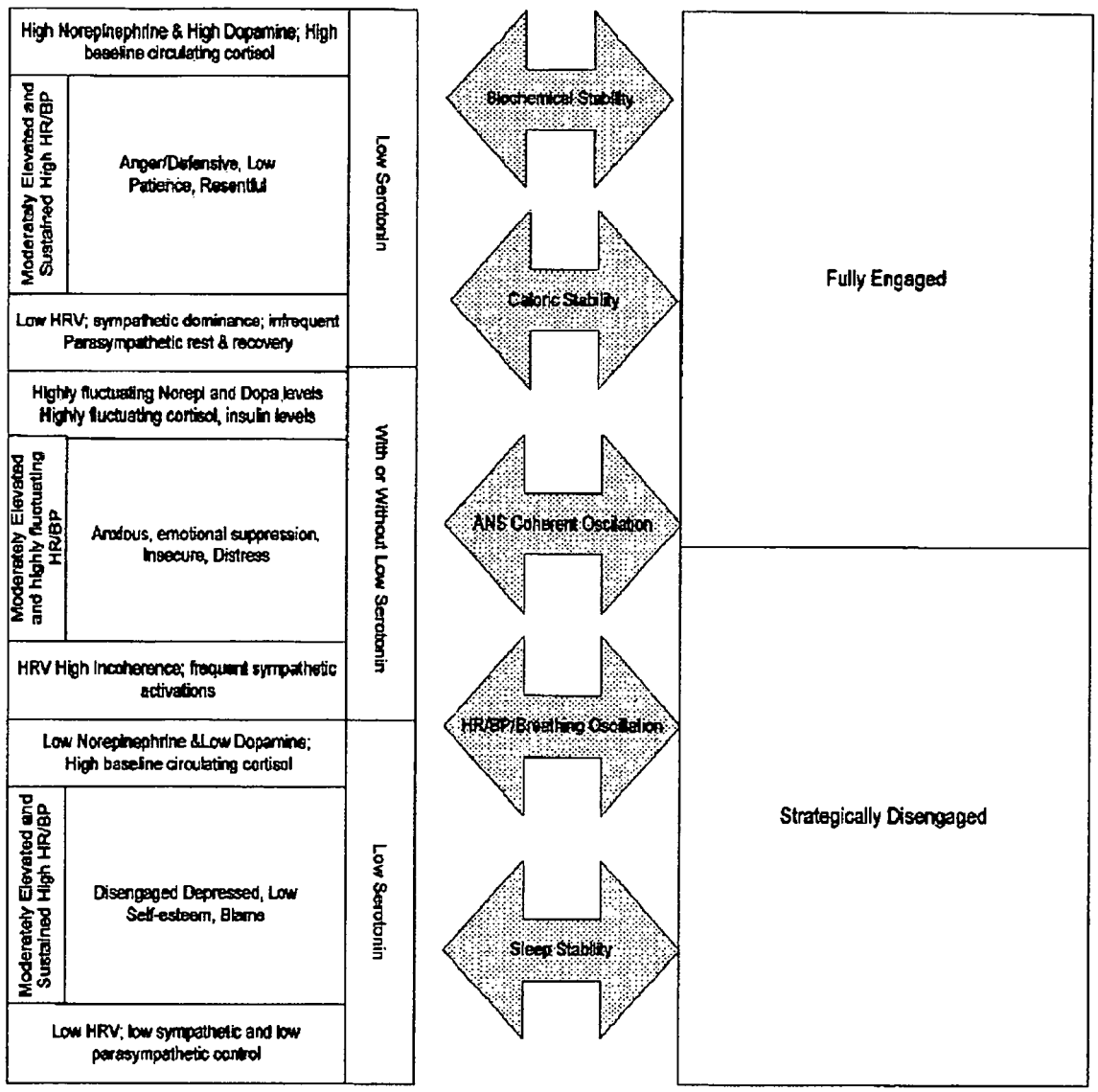
FIG. 20 illustrates various physiological aspects that can be monitored.

FIG. 19 illustrates generally an example of an external device 900. Upon reading and comprehending the content of this disclosure, one of ordinary skill in the art will understand the manner in which a software program can be launched from a computer-readable medium in a computer-based system to execute the functions defined in the software program. One of ordinary skill in the art will further understand the various programming languages that can be employed to create one or more software programs designed to implement and perform the methods disclosed herein. The programs can be structured in an object-orientated format using an object-oriented language, such as Java, C++, or one or more other languages. Alternatively, the programs can be structured in a procedure-orientated format using a procedural language, such as assembly, C, etc. The software components can communicate using any of a number of mechanisms well known to those of ordinary skill in the art, such as application program interfaces or interprocess communication techniques, including remote procedure calls or others. The teachings of various embodiments are not limited to any particular programming language or environment.

Thus, other embodiments can be realized. For example, an article of manufacture, such as a computer, a memory system, a magnetic or optical disk, some other storage device, or any type of electronic device or system can include one or more processors 902 coupled to a computer-readable medium 922 such as a memory (e.g., removable storage media, as well as any memory including an electrical, optical, or electromagnetic conductor) having instructions 924 stored thereon (e.g., computer program instructions), which when executed by the one or more processors 902 result in performing any of the actions described with respect to the methods above.

External device 900 can take the form of a computer system having a processor 902 coupled to a number of components directly, and/or using a bus 908. Such components can include main memory 904, static or non-volatile memory 906, and mass storage 916. Other components coupled to the processor 902 can include an output device 910, such as a video display, an input device 912, such as a keyboard, and a cursor control device 914, such as a mouse. A network interface device 920 to couple the processor 902 and other components to a network 926 can also be coupled to the bus 908. The instructions 924 can further be transmitted or received over the network 926 via the network interface device 920 utilizing any one of a number of well-known transfer protocols (e.g., HTTP). Any of these elements coupled to the bus 908 can be absent, present singly, or present in plural numbers, depending on the specific embodiment to be realized.

In an example, one or more of the processor 902, the memories 904, 906, or the storage device 916 can each include instructions 924 that, when executed, can cause external device 900 to perform any one or more of the methods described herein. In alternative embodiments, external device 900 operates as a standalone device or can be connected (e.g., networked) to other devices. In a networked environment, external device 900 can operate in the capacity of a server or a client device in server-client network environment, or as a peer device in a peer-to-peer (or distributed) network environment. Monitor unit 900 may include a computer such as a personal computer (PC), a tablet PC, a set-top box (STB), a Personal Digital Assistant (PDA), a cellular telephone, a web appliance, a network router, switch or bridge, or any device capable of executing a set of instructions (sequential or otherwise) that specify actions to be taken by that device. Further, the term "computer" shall also be taken to include any collection of devices that individually or jointly execute a set (or multiple sets) of instructions to perform any one or more of the methodologies discussed herein.

External device 900 also includes a sensor interface 928 for communicating with sensor module 930 using one or more wireless communication protocols (e.g., WiFi, ZigBee, etc.) In one example embodiment, external device 900 communicates with sensor module 930 via inductive coupling.

While the computer-readable medium 924 is shown as a single medium, the term "computer-readable medium" should be taken to include a single medium or multiple media (e.g., a centralized or distributed database, or associated caches and servers, and or a variety of storage media, such as the processor 902 registers, memories 904, 906, and the storage device 916) that store the one or more sets of instructions 924. The term "computer-readable medium" shall also be taken to include any medium that is capable of storing, encoding or carrying a set of instructions for execution by the computer and that cause the computer to perform any one or more of the methodologies of the present invention, or that is capable of storing, encoding or carrying data structures utilized by or associated with such a set of instructions. The term "computer-readable medium" shall accordingly be taken to include, but not be limited to tangible media, such as solid-state memories, optical, and magnetic media.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method for monitoring an individual's autonomic nervous system (ANS), the method comprising:
   providing a sensor module, wherein the sensor module includes a cardiac sensor;
   mounting the sensor module in a sensor platform, wherein the sensor platform includes an adhesive side, a release sheet protecting the adhesive side and a pocket, wherein the pocket is designed to receive the sensor module, to facilitate sensing by the cardiac sensor of heart rate activity, and to allow insertion and removal of the sensor module from the pocket, removing the pocket adhesive release sheet and closing the pocket with the pocket adhesive;
   attaching the sensor platform to an individual; wherein attaching includes removing the sensor platform release sheet to expose the adhesive side and affixing the platform to the individual via the adhesive side;
   capturing the individual's heart rate activity data from the cardiac sensor and processing the heart rate activity data to capture a pattern of ANS activity during an experience of a stimulus and a pattern of ANS activity after an experience of a stimulus;
   characterizing variability, parasympathetic gain, or parasympathetic control of the captured heart rate activity;
   quantifying and characterizing oscillation of the captured heart rate activity and assessing autonomic tone, coherence, or entrainment;
   capturing movement data from a sensor and processing the movement data to deduce an effect of movement on the heart rate activity;
   assessing changes between the ANS pattern during the stimulus and the ANS pattern after the stimulus; and
   providing feedback.

2. The method of claim 1, wherein the method further comprises contextualizing the ANS data to an aspect associated with the experience including one or more of the following: a biological rhythm; an aspect of nutritional intake or energy expenditure; an aspect of a sleep/rest pattern; a stress management activity; a relaxation activity; a stress resilience or strength building activity; a breathing pattern; a mind/body activity; a cognitive appraisal or emotional processing activity; a biofeedback activity; an exercise or a physical activity; a movement; recovery from an exercise, physical activity, or a movement; hydration level; an aspect of a biochemical messenger; an underlying medical condition; genomic or proteomic information; a psychological, physiological, chemical, social or environmental stimulus encountered by the individual; a biological pathway; a measurement of parasympathetic tone or entrainment; an ANS pattern of physiological balance, imbalance, coherence, incoherence, stress, recovery, resilience, or entrainment; resting or nighttime heart rate variability (HRV); heart rate or heart rate recovery; increasing heart rate variability; an activity; a physiological aspect of the individual; an aspect of time, location, or the environment; a behavior; a pattern of daily living; a weight management activity; a measured effect on physiology; a stimulant or a suppressant; a blood pressure measurement; a cortisol measurement; a measurement of sympathetic tone; a respiratory measurement; a cholesterol measurement; a glucose measurement; an insulin measurement; a medication.

3. The method claim 1, wherein the method further comprises providing feedback on one or more of the following: an intensity, a duration, a resilience, an oscillatory characteristic, or a speed of recovery of an ANS activation or recovery pattern in response to a stimulus; autonomic tone or resilience; entrainment between the parasympathetic and sympathetic branches; variability between the parasympathetic and sympathetic branches; coherence between the parasympathetic and sympathetic branches; an assessment of physiological balance, imbalance, coherence, incoherence, or entrainment; a strategy or a recommendation to change a physiological or psychological pattern; an effect of a strategy or a recommendation on a physiological or psychological pattern; a strategy to change a behavior, an underlying belief, or a neural pathway; an effect of a strategy to change a behavior, an underlying belief, or a neural pathway; a characterization of a mental, emotional, or physiological state of the individual; a contextual aspect surrounding the physiological data; a triggering event causing a stress pattern; an effectiveness or a resilience of a physiological pathway; a cause and effect correlation of a stress or a resilience activity on mood, cognitive performance, vitality, or a health condition; an alert to build parasympathetic tone, control, or resilience at a specific time or for a specific duration; diagnostic or treatment information for: an immune state, an inflammatory state, a metabolic state, a mental health state, a chronic disease state, an addictive disorder, a vulnerable population, medication management, personalized medicine, an effect of the environment on physiology, electromagnetic interference or radiation exposure, resiliency training, changing neural pathways or neurotransmitters.

4. A method for monitoring a pattern of an individual's autonomic nervous system (ANS) activity surrounding an experience, the method comprising:
providing a sensor module, wherein the sensor module includes a cardiac sensor;
mounting the sensor module in a sensor platform, wherein the sensor platform includes an adhesive side, a release sheet protecting the adhesive side and a pocket, wherein the pocket is designed to receive the sensor module, to facilitate sensing by the cardiac sensor of heart rate activity, and to allow insertion and removal of the sensor module from the pocket; wherein the sensor platform further includes a pocket adhesive protected by an adhesive release sheet; and wherein mounting includes inserting the sensor module into the pocket, removing the pocket adhesive release sheet and closing the pocket with the pocket adhesive;
attaching the sensor platform to an individual; wherein attaching includes removing the sensor platform release sheet to expose the adhesive side and affixing the platform to the individual via the adhesive side;
capturing the individual's heart rate activity data from the cardiac sensor and processing the heart rate activity data to capture a pattern of the individual's nervous system activity surrounding an experience
characterizing variability of the captured heart rate activity;
quantifying and characterizing oscillation of the captured heart rate activity and assessing autonomic tone, coherence, or entrainment;
capturing movement data from a sensor and processing the movement data to deduce an effect of movement on the heart rate activity; and
providing feedback.

5. The method of claim 4, wherein the method further comprises contextualizing the ANS data to an aspect associated with the experience including one or more of the following: a biological rhythm; an aspect of nutritional intake or energy expenditure; an aspect of a sleep/rest pattern; a stress management activity; a relaxation activity; a stress resilience or strength building activity; a breathing pattern; a mind/body activity; a cognitive appraisal or emotional processing activity; a biofeedback activity; an exercise or a physical activity; a movement; recovery from an exercise, physical activity, or a movement; hydration level; an aspect of a biochemical messenger; an underlying medical condition; genomic or proteomic information; a psychological, physiological, chemical, social or environmental stimulus encountered by the individual; a biological pathway; a measurement of parasympathetic tone or entrainment; an ANS pattern of physiological balance, imbalance, coherence, incoherence, stress, recovery, resilience, or entrainment; resting or nighttime heart rate variability (HRV); heart rate or heart rate recovery; increasing heart rate variability; an activity; a physiological aspect of the individual; an aspect of time, location, or the environment; a behavior; a pattern of daily living; a weight management activity; a measured effect on physiology; a stimulant or a suppressant; a blood pressure measurement; a cortisol measurement; a measurement of sympathetic tone; a respiratory measurement; a cholesterol measurement; a glucose measurement; an insulin measurement; a medication.

6. The method claim 4, wherein the method further comprises providing feedback on one or more of the following: an intensity, a duration, a resilience, an oscillatory characteristic, or a speed of recovery of an ANS activation or recovery pattern in response to a stimulus; autonomic tone or resilience; entrainment between the parasympathetic and sympathetic branches; variability between the parasympathetic and sympathetic branches; coherence between the parasympathetic and sympathetic branches; an assessment of physiological balance, imbalance, coherence, incoherence, or entrainment; a strategy or a recommendation to change a physiological or psychological pattern; an effect of a strategy or a recommendation on a physiological or psychological, pattern; a strategy to change a behavior, an underlying belief, or a neural pathway; an effect of a strategy to change a behavior, an underlying belief, or a neural pathway; a characterization of a mental, emotional, or physiological state of the individual; a contextual aspect surrounding the physiological data; a triggering event causing a stress pattern; an effectiveness or a resilience of a physiological pathway; a cause and effect correlation of a stress or a resilience activity on mood, cognitive performance, vitality, or a health condition; an alert to build parasympathetic tone, control, or resilience at a specific time or for a specific duration; diagnostic or treatment information for: an immune state, an inflammatory state, a metabolic state, a mental health state, a chronic disease state, an addictive disorder, a vulnerable population, medication management, personalized medicine, an effect of the environment on physiology, electromagnetic interference or radiation exposure, resiliency training, changing neural pathways or neurotransmitters.

* * * * *